(12) United States Patent
Thomas et al.

(10) Patent No.: US 8,772,047 B2
(45) Date of Patent: Jul. 8, 2014

(54) DYES HAVING RATIOMETRIC FLUORESCENCE RESPONSE FOR DETECTING METABOLITES

(75) Inventors: Joseph Thomas, Raleigh, NC (US); Michael T. Cash, Timberlake, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 971 days.

(21) Appl. No.: 12/124,553

(22) Filed: May 21, 2008

(65) Prior Publication Data

US 2008/0311675 A1  Dec. 18, 2008

Related U.S. Application Data

(60) Provisional application No. 60/939,507, filed on May 22, 2007.

(51) Int. Cl.
*G01N 33/533* (2006.01)
*G01N 33/53* (2006.01)
*C12M 1/34* (2006.01)
*G01N 33/58* (2006.01)
*A61K 8/49* (2006.01)

(52) U.S. Cl.
CPC ............. *G01N 33/582* (2013.01); *A61K 8/498* (2013.01); *C12M 1/34* (2013.01); *G01N 33/53* (2013.01)
USPC .......................... 436/546; 435/7.1; 435/287.2

(58) Field of Classification Search
CPC ........ G01N 33/582; A61K 8/498; C12M 1/34
See application file for complete search history.

(56) References Cited

U.S. PATENT DOCUMENTS

| | | | |
|---|---|---|---|
| 3,964,871 | A | 6/1976 | Hochstrasser |
| 4,981,779 | A | 1/1991 | Wagner |
| 5,001,054 | A | 3/1991 | Wagner |
| 5,246,867 | A | 9/1993 | Lakowicz et al. |
| 5,712,223 | A | 1/1998 | DeBoer et al. |
| 6,192,891 | B1 | 2/2001 | Gravel et al. |
| 6,197,534 | B1 | 3/2001 | Lakowicz et al. |
| 6,277,627 | B1 | 8/2001 | Hellinga |
| D491,275 | S | 6/2004 | Walters et al. |
| 6,855,556 | B2 | 2/2005 | Amiss et al. |
| 6,922,576 | B2 | 7/2005 | Raskas |
| 7,064,103 | B2 | 6/2006 | Pitner et al. |
| D545,439 | S | 6/2007 | Draudt et al. |
| 7,563,891 | B2 * | 7/2009 | Pitner et al. .................... 544/105 |
| 2003/0153012 | A1 | 8/2003 | Renard et al. |
| 2003/0165942 | A1 | 9/2003 | Czerney et al. |
| 2004/0118681 | A1 | 6/2004 | Hellinga et al. |
| 2005/0014290 | A1 | 1/2005 | Hsieh et al. |
| 2005/0042704 | A1 | 2/2005 | Alarcon et al. |
| 2005/0113657 | A1 | 5/2005 | Alarcon et al. |
| 2005/0113658 | A1 | 5/2005 | Jacobson et al. |
| 2005/0240119 | A1 | 10/2005 | Draudt et al. |
| 2006/0078908 | A1 | 4/2006 | Pitner et al. |
| 2006/0166368 | A1 | 7/2006 | Berkelman |
| 2006/0280652 | A1 | 12/2006 | Pitner et al. |
| 2008/0044856 | A1 | 2/2008 | Amiss et al. |

FOREIGN PATENT DOCUMENTS

| | | |
|---|---|---|
| EP | 1 318 177 A2 | 6/2003 |
| EP | 1 318 177 B1 | 6/2003 |
| EP | 1 535 969 A2 | 6/2005 |
| EP | 1 535 969 A3 | 6/2005 |
| JP | 2007-55956 | 3/2007 |
| WO | WO 96/33412 A1 | 10/1996 |
| WO | WO 03/057851 | 7/2003 |
| WO | WO 2006/025887 A2 | 3/2006 |
| WO | WO 2006/025887 A3 | 3/2006 |

OTHER PUBLICATIONS

De Lorimier et al. Construction of a fluorescent biosensor family. Protein Science 2002, vol. 11, pp. 2655-2675.*
De Lorimier, R. M., et al., "Construction of a Fluorescent Biosensor Family," *Protein Science*, 2002, vol. 11, No. 11, pp. 2655-2675.
Looger, L. L., et al., "Computational Design of Receptor and Sensor Proteins with Novel Functions," *Nature*, 2003, vol. 423, No. 6936, pp. 185-190.
Rattan et al., "Protein Synthesis, Posttranslational Modifications, and Aging," *Ann NY Acad Sci.*, 1992, vol. 663, pp. 48-62.
Renard, M. and Bedouelle H., "Improving the Sensitivity and Dynamic Range of Reagentless Fluorescent Immunosensors by Knowledge-Based Design," *Biochemistry*, 2004, vol. 43, No. 49, pp. 15453-15462.
Richieri, G.V., et al., "A Fluorescently Labeled Intestinal Fatty Acid Binding Protein—Interactions with Fatty Acids and its Use in Monitoring Free Fatty Acids," *J. Biol. Chem.*, 1992, vol. 267, No. 33, pp. 23495-23501.
Seifter, S. and England, S., "Analysis for Protein Modifications and Nonprotein Cofactors," *Methods in Enzymology*, 1990, vol. 182, pp. 626-646.
Smith, E. R. and Storch, J., "The Adipocyte Fatty Acid-binding Protein Binds to Membranes by Electrostatic Interactions," *J. Biol. Chem.*, 1999, vol. 274, No. 50, pp. 35325-35330.
Wold, F., "Posttranslational Protein Modifications: Perspectives and Prospects," in *Posttranslational Covalent Modification of Proteins*, B. C. Johnson, Ed., Academic Press, New York (1983).
Janecki, T. and Bodalski, R., "A Convenient Horner-Emmons Approach to the Synthesis of Substituted Ethyl 1, 3-Butadiene-2-Carboxylates, and Related Compounds," *Synthesis*, 1989, pp. 506-510, No. 7. Tkach, I. I., et al., "Synthesis, Luminescence, and Spectral Characteristics of 7-Diethylamino-3-(2-Arylethenyl)Coumarins," *Chemistry of Heterocyclic Compounds*, 1992, pp. 985-989, vol. 28, No. 9.

(Continued)

*Primary Examiner* — Shafiqul Haq
(74) *Attorney, Agent, or Firm* — Alston & Bird LLP

(57) ABSTRACT

The presently disclosed subject matter provides thiol-reactive, environmentally sensitive fluorescent dyes, or fluorophores, which have an emission wavelength in the visible spectral region. When conjugated with a binding protein, the fluorophores exhibit a ratiometric response to one or more ligands or target analytes. The presently disclosed fluorophore-binding protein conjugates can be used to detect the presence of or amount of physiologically-important metabolites, such as glucose, fatty acids, and lactate, in biological samples.

30 Claims, 17 Drawing Sheets

(56) References Cited

OTHER PUBLICATIONS

Xu, L.-H., et al., "Synthesis of Styrylcoumarins from Coumarin Diazonium Salts and Studies of Their Spectra Characteristics," *Dyes and Pigments*, 2004, pp. 283-289, vol. 62, No. 3.

Alexeev, V., et al., "Photonic Crystal Glucose-Sensing Material for Noninvasive Monitoring of Glucose in Tear Fluid," *Clinical Chemistry*, 2004, pp. 2353-2360, vol. 50, No. 12.

Long, J. et al., "Synthesis and Fluorescence Properties of Novel Benzo[a]phenoxazine-5-one Derivatives," *J. Heterocyclic Chem.*, 1999, pp. 895-899, vol. 36.

Richieri, G.V., et al., "A Fluorescently Labeled Intestinal Fatty Acid Binding Protein—Interactions with Fatty Acids and Its Use in Monitoring Free Fatty Acids," *J. Biol. Chem.*, 1992, pp. 23495-23501, vol. 267, No. 33.

\* cited by examiner

DYES HAVING RATIOMETRIC FLUORESCENCE RESPONSE FOR DETECTING METABOLITES

CROSS REFERENCE TO RELATED APPLICATION

This application claims the benefit of U.S. Provisional Application No. 60/939,507, filed on May 22, 2007, which is herein incorporated by reference in its entirety.

FIELD OF THE INVENTION

The presently disclosed subject matter relates to fluorescent dyes, conjugates thereof, and their use for detecting one or more metabolites in a biological sample.

BACKGROUND

The detection of physiologically-important molecules, such as metabolites, in a biological sample can be critical for monitoring a condition or a disease state of a subject. For example, the monitoring of glucose can be used to diagnose and manage diabetes, wherein maintaining blood glucose within a normal range of 70 to 120 mg/dL with insulin therapy and increased glucose monitoring can improve the long-term prognosis of subjects suffering from diabetes. Glucose levels alone, however, do not provide sufficient information for understanding the metabolic processes underlying diabetes and its development. The monitoring of fatty acids can provide an additional understanding of the events leading to the development of a pre-diabetic state or insulin resistance in a subject suffering from diabetes, particularly Type 2 diabetes. Similarly, energy metabolites, such as lactate, a byproduct of moderate exercise, can be monitored to assess the energy expenditure, exercise burden, or fatigue level of a subject.

One method for detecting metabolites, such as glucose, fatty acids, and lactate, includes conjugating a fluorophore, such as a fluorescent dye, with a binding member, i.e., a binding member of a specific binding pair, that has an affinity and specificity for a ligand, e.g., a metabolite of interest, and measuring a change in a fluorescent property of the fluorophore upon ligand binding. There is a need in the art, however, for improved fluorescent dyes for use as fluorophores in such systems. The presently disclosed subject matter addresses, in whole or in part, these and other needs in the art.

SUMMARY

The presently disclosed subject matter provides thiol-reactive, environmentally sensitive fluorescent dyes, or fluorophores, which have an emission wavelength in the visible spectral region and exhibit a ratiometric response to one or more ligands or target analytes. In some embodiments, the presently disclosed fluorophores have the following general formula:

A-Y wherein:
A is selected from the group consisting of a coumarin nucleus and an aza-coumarin nucleus;
Y is selected from the group consisting of:

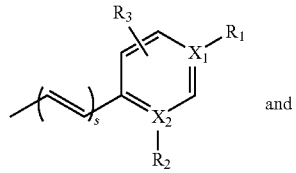

and

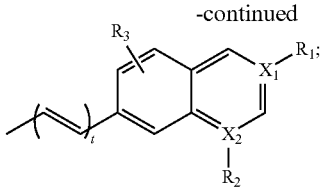

-continued wherein:
s and t are each independently an integer from 1 to 8;
each $X_1$ and $X_2$ is independently selected from the group consisting of C, S, and N, wherein at least one of $X_1$ and $X_2$ is N, under the proviso that (i) when $X_1$ is C or S, $R_1$ is Z, or when $X_2$ is C or S, $R_2$ is Z, as Z is defined herein below; (ii) if both $X_1$ and $X_2$ are N at the same time, at least one of $R_1$ and $R_2$ is absent; and (iii) when $X_1$ is N, $R_1$ when present is Z', or when $X_2$ is N, $R_2$ when present is Z', wherein Z' is selected from the group consisting of:

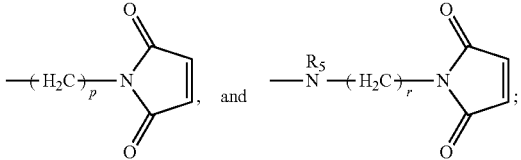

wherein:
n, p, and r are each independently an integer from 1 to 8;
$X_3$ is O or $NR_6$;
each $R_3$, $R_5$, $R_6$ and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;
$R_4$ is —$(CH_2)_m$—$X_4$;
wherein m is an integer from 1 to 8; and
$X_4$ is halogen.

In some embodiments, the presently disclosed fluorescent dyes can be conjugated with another molecule, such as a member of a specific binding pair, which has an affinity for a specific ligand or analyte. Such conjugates can be used as a biosensor compound to detect a metabolite of interest. Accordingly, in some embodiments, the presently disclosed subject matter provides a biosensor compound having the formula:

A-Y'—B wherein:
A is selected from the group consisting of a coumarin nucleus and an aza-coumarin nucleus;
Y' is selected from the group consisting of:

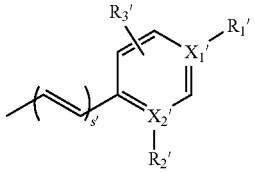

and

-continued

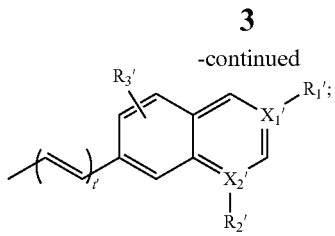

wherein:
s' and t' are each independently an integer from 1 to 8;
each $X_1'$ and $X_2'$ is independently selected from the group consisting of C, S, and N, wherein at least one of $X_1'$ and $X_2'$ is N, under the proviso that (i) when $X_1'$ is C or S, $R_1'$ is Z, or when $X_2'$ is C or S, $R_2'$ is Z, as Z is defined herein below; (ii) if both $X_1'$ and $X_2'$ are N at the same time, at least one of $R_1'$ and $R_2'$ is absent; and (iii) when $X_1'$ is N, $R_1'$ when present is Z', or when $X_2'$ is N, $R_2'$ when present is Z'', wherein Z'' is selected from the group consisting of:

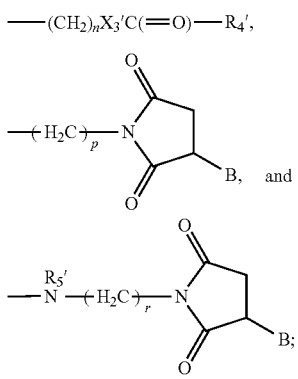

wherein:
n, p, and r are each independently an integer from 1 to 8;
$X_3'$ is O or $NR_6'$;
each $R_3'$, $R_5'$, $R_6'$ and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;
$R_4'$ is —$(CH_2)_m$—B;
wherein m is an integer from 1 to 8; and
B is a binding member having a binding affinity for a ligand or analyte to be detected; and
wherein the biosensor compound exhibits a detectable change in a fluorescence property as a result of binding to the ligand or analyte or as a result of a change in concentration of the ligand or analyte in a sample under test.

In some embodiments, the presently disclosed subject matter provides a method for determining the presence or amount of one or more analytes in a sample, the method comprising: (a) providing a biosensor compound of formula A-Y'—B having at least one mutated binding protein with a fluorophore covalently attached thereto through a thiol group of the mutated binding protein; (b) contacting the biosensor compound with a sample suspected of containing one or more analytes to bind the one or more analytes, if present, with the binding protein; (c) irradiating the sample suspected of containing one or more analytes with electromagnetic radiation to induce the fluorophore to fluoresce; and (d) detecting a fluorescence property to determine the presence or amount of the one or more analytes in the sample.

In some embodiments, the presently disclosed subject matter provides a biosensor device comprising a biosensor compound of formula A-Y'—B. In some embodiments, the presently disclosed subject matter provides a reagent for determining the presence or amount of one or more analytes in a sample, the reagent comprising a biosensor compound of formula A-Y'—B. In some embodiments, the presently disclosed subject matter provides a kit for determining the presence or amount of one or more analytes in a sample, the kit comprising a biosensor compound of formula A-Y'—B.

Certain objects of the presently disclosed subject matter having been stated hereinabove are addressed in whole or in part by the presently disclosed subject matter; other objects will become evident as the description proceeds when taken in connection with the accompanying Examples and Drawings as best described herein below.

BRIEF DESCRIPTION OF THE DRAWINGS

Figure 4:
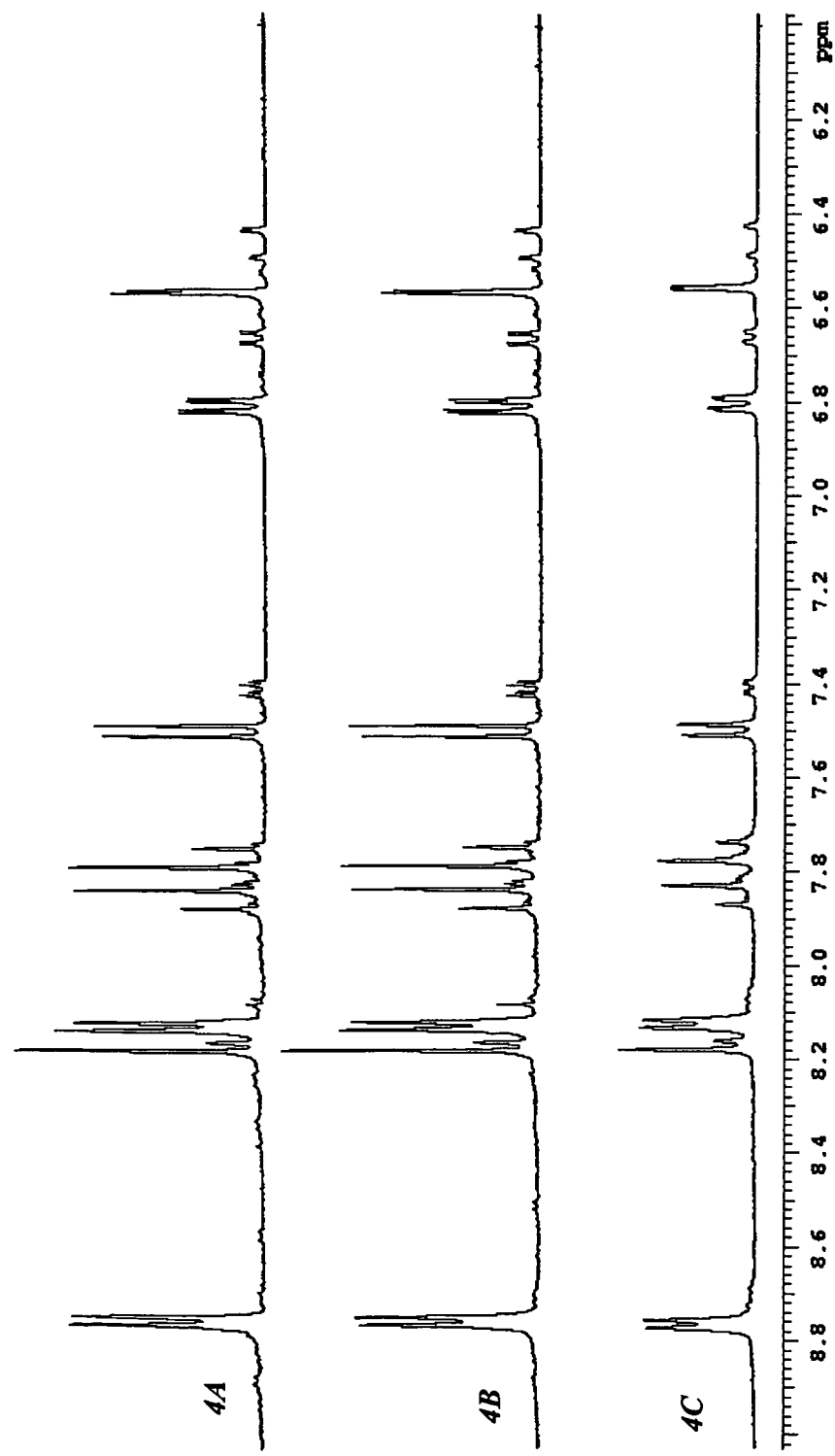
Figure 5:
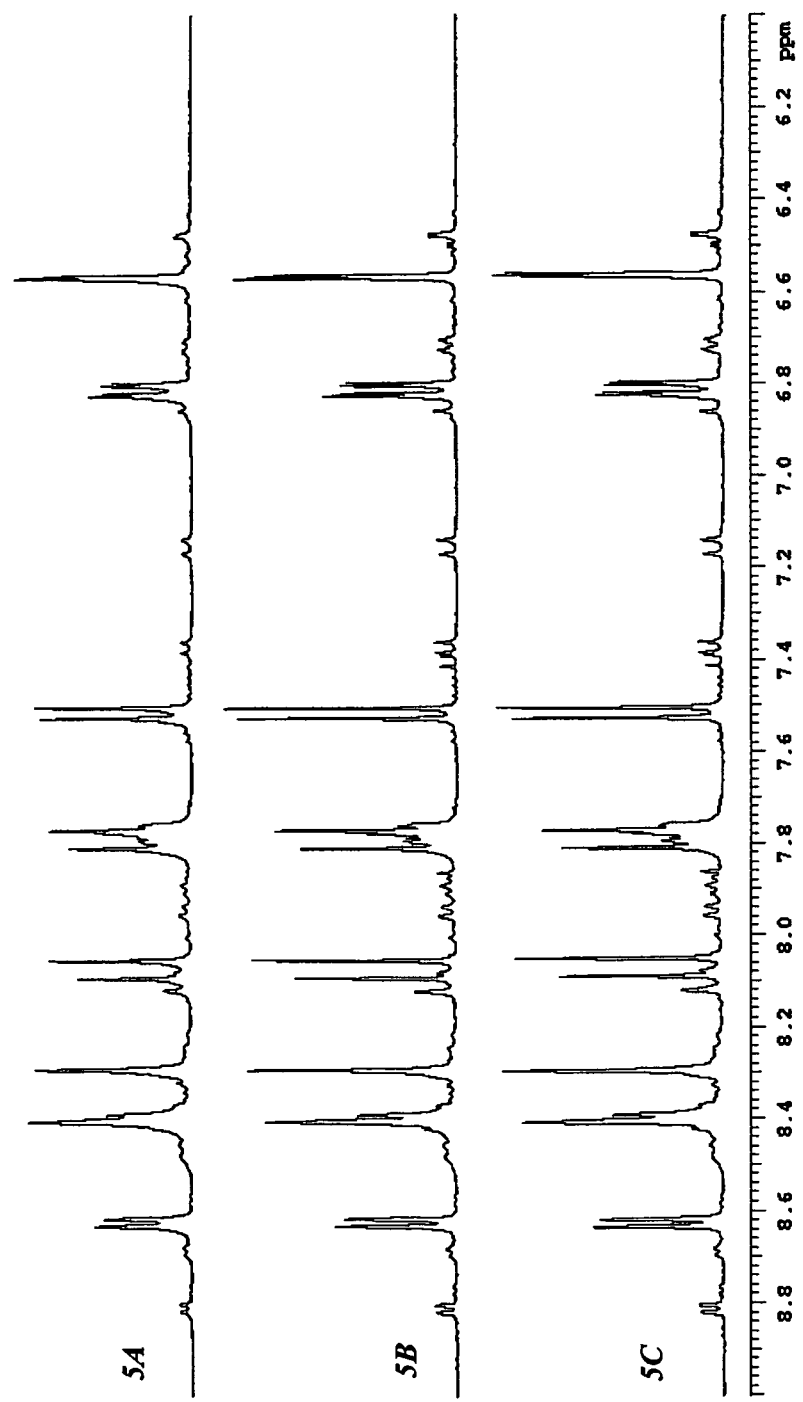
Figure 6:
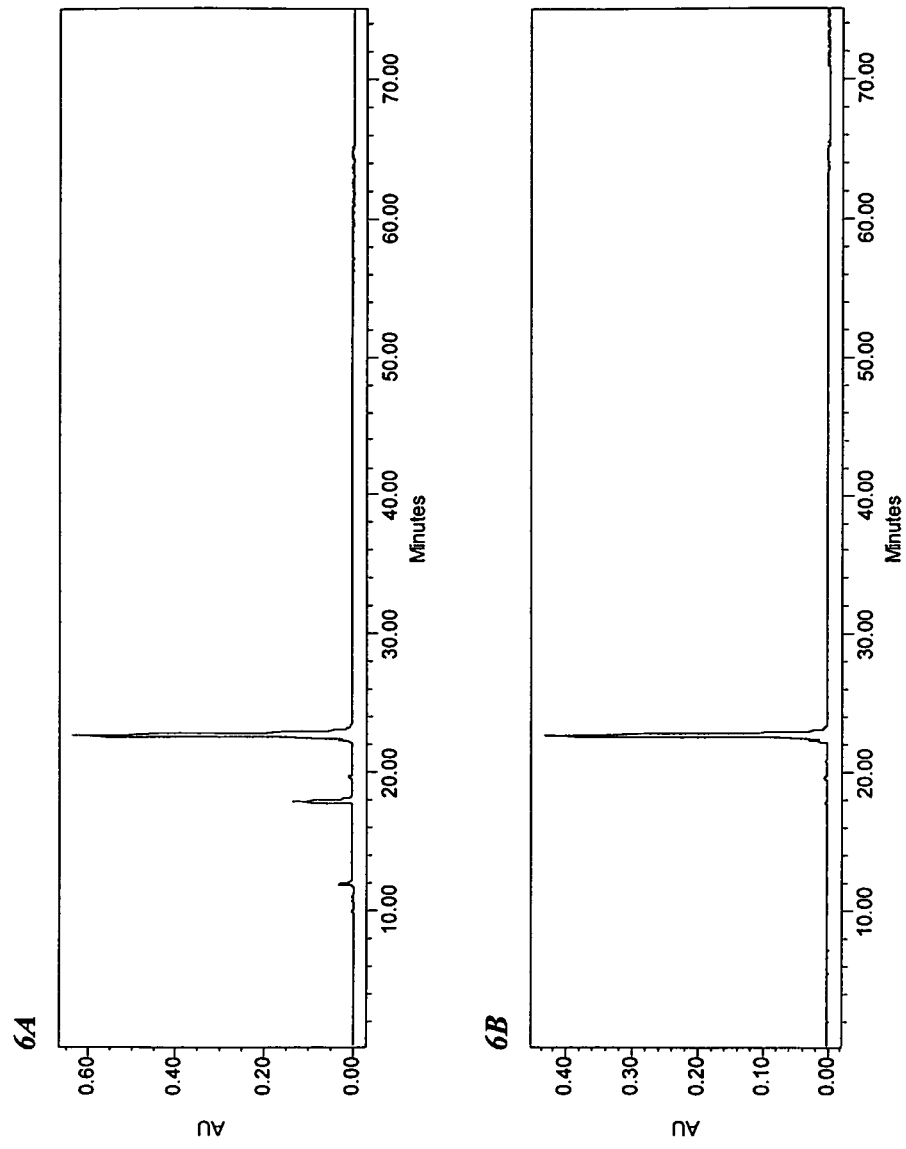
Figure 7:
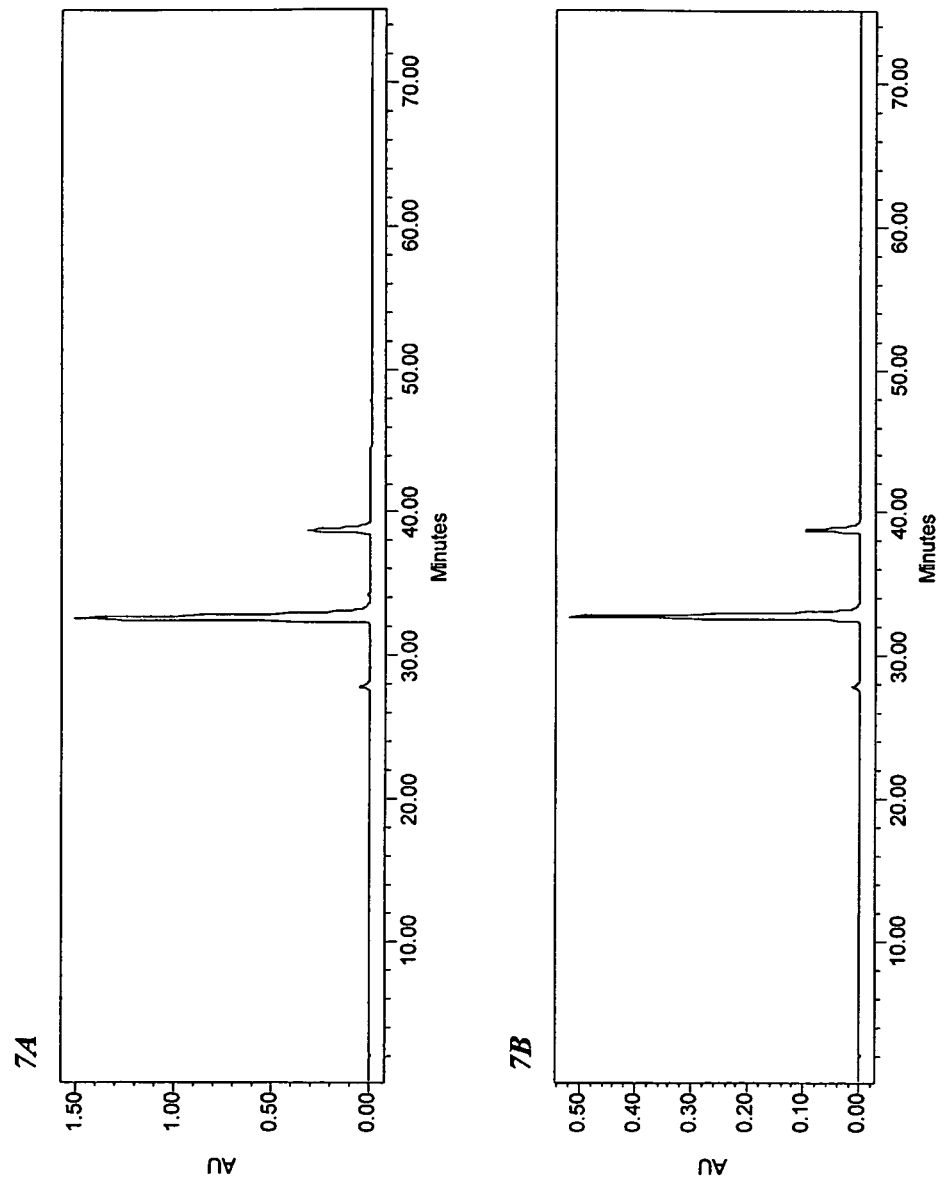
Figure 8:
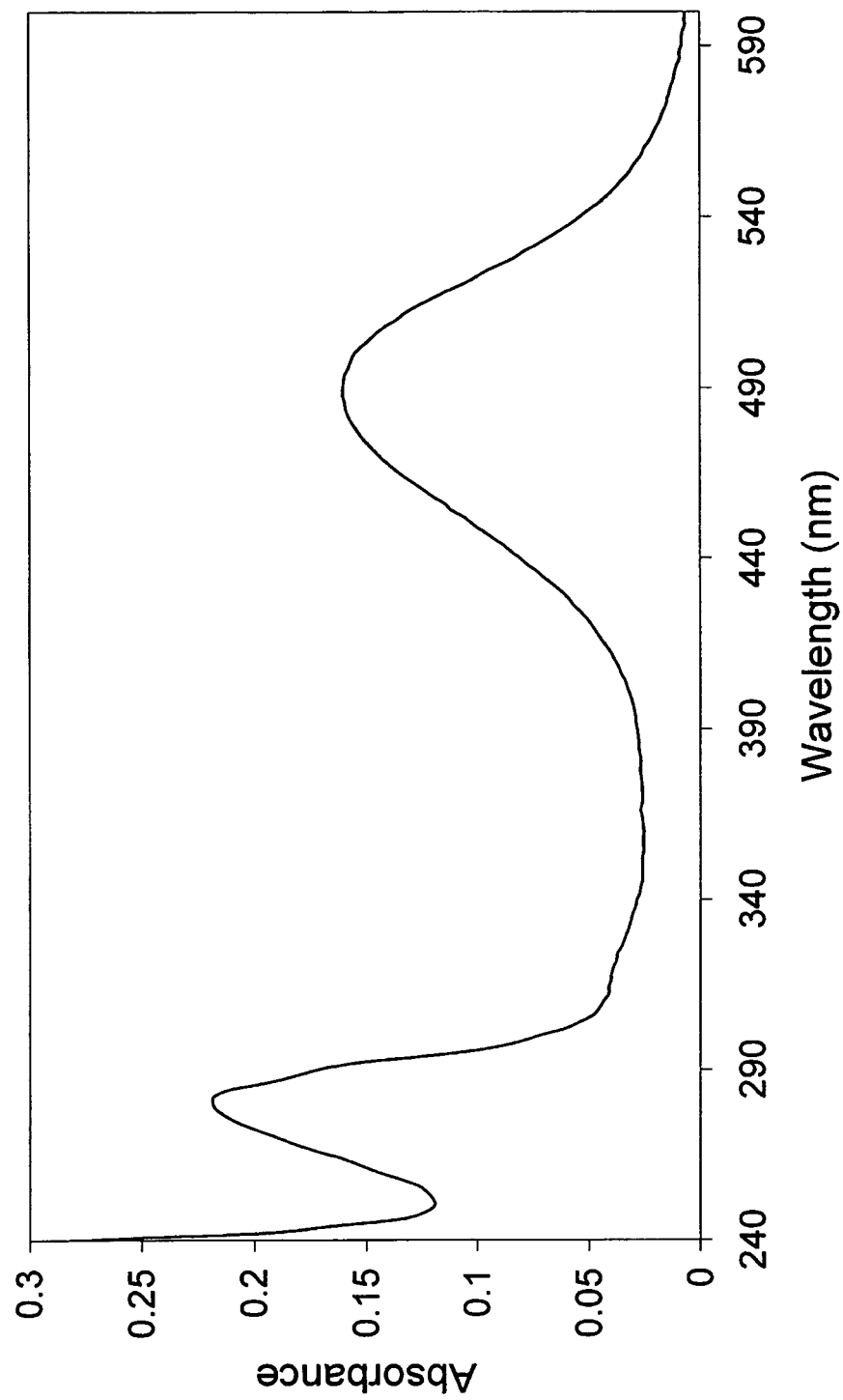
Figure 9A:
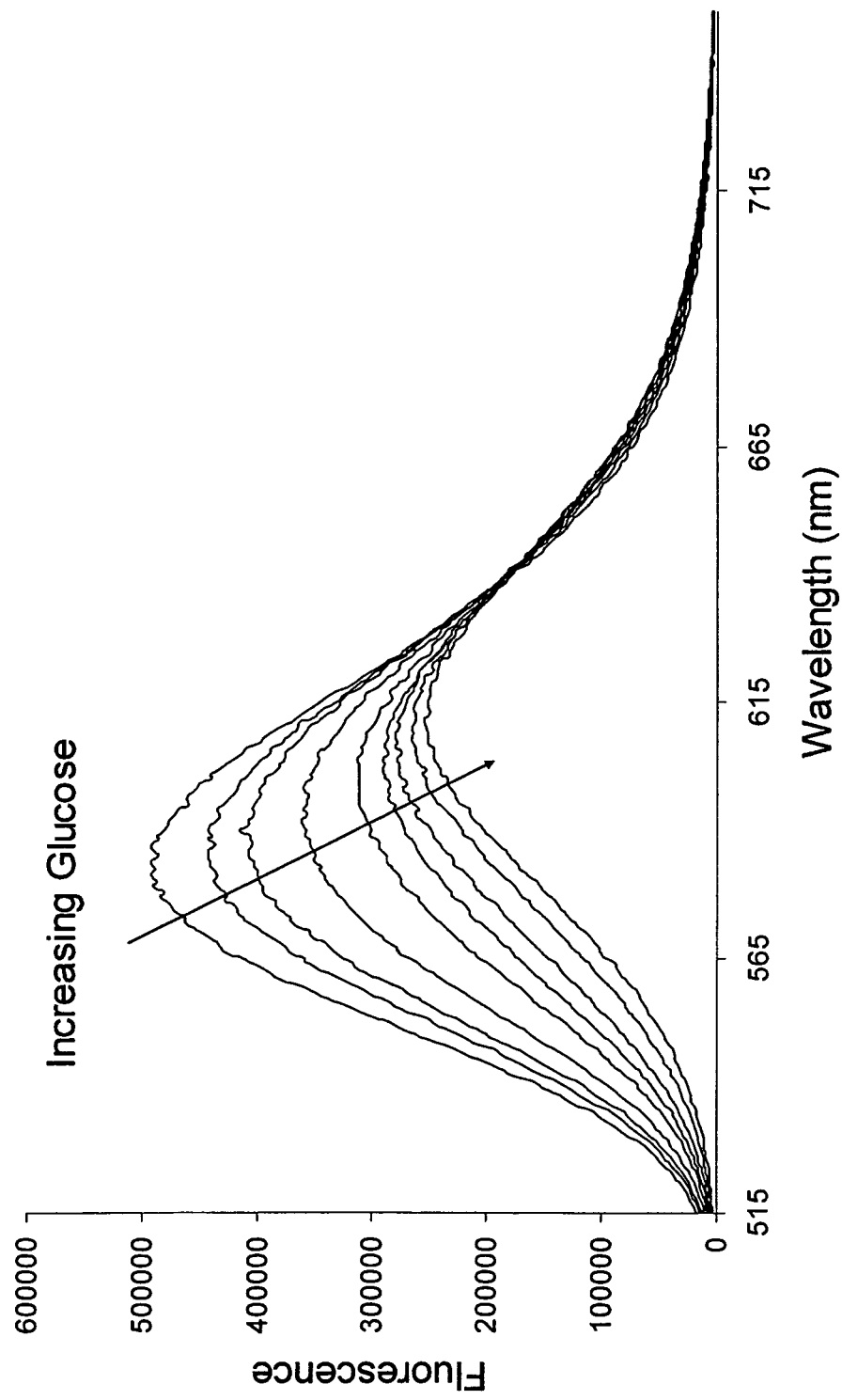
Figure 9B:
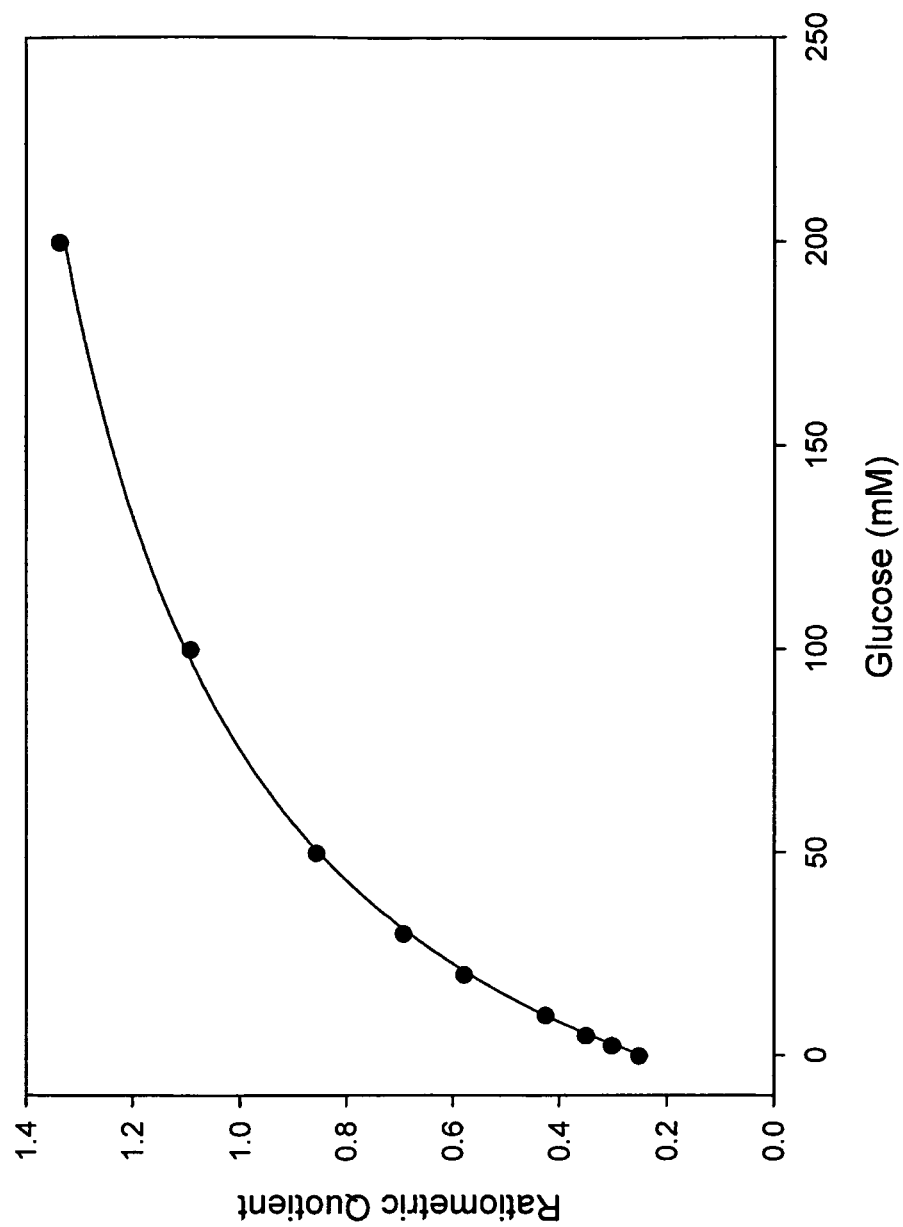
Figure 10:
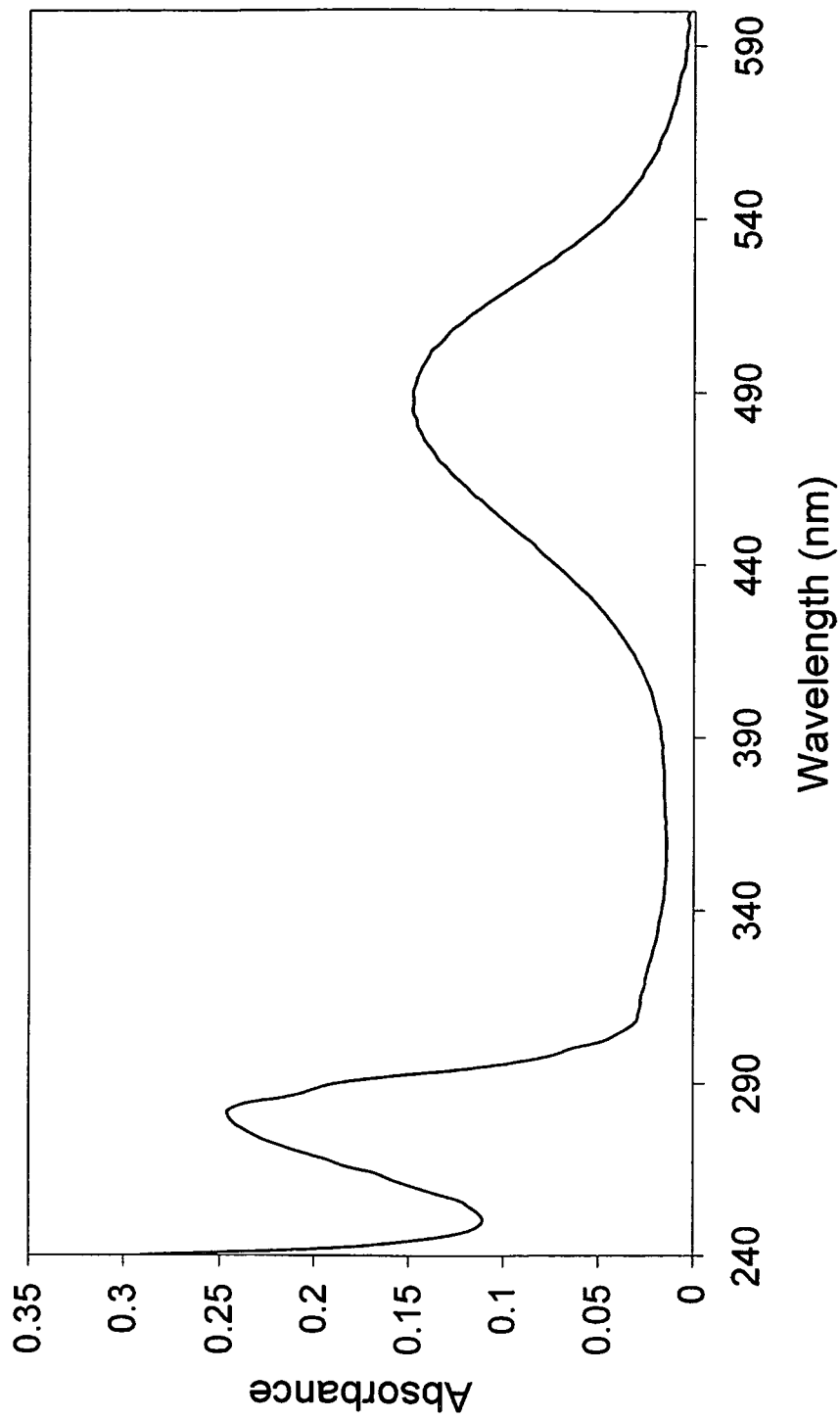
Figure 11A:
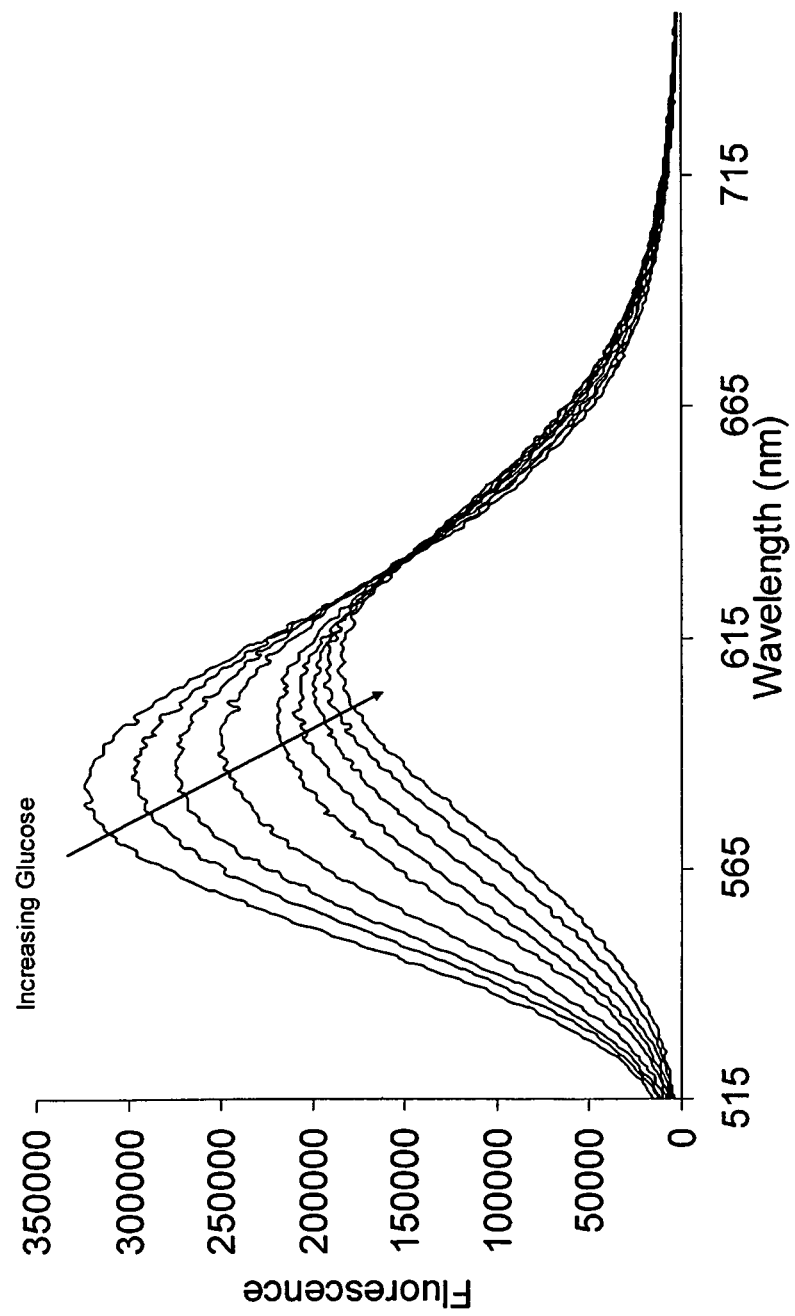
Figure 11B:
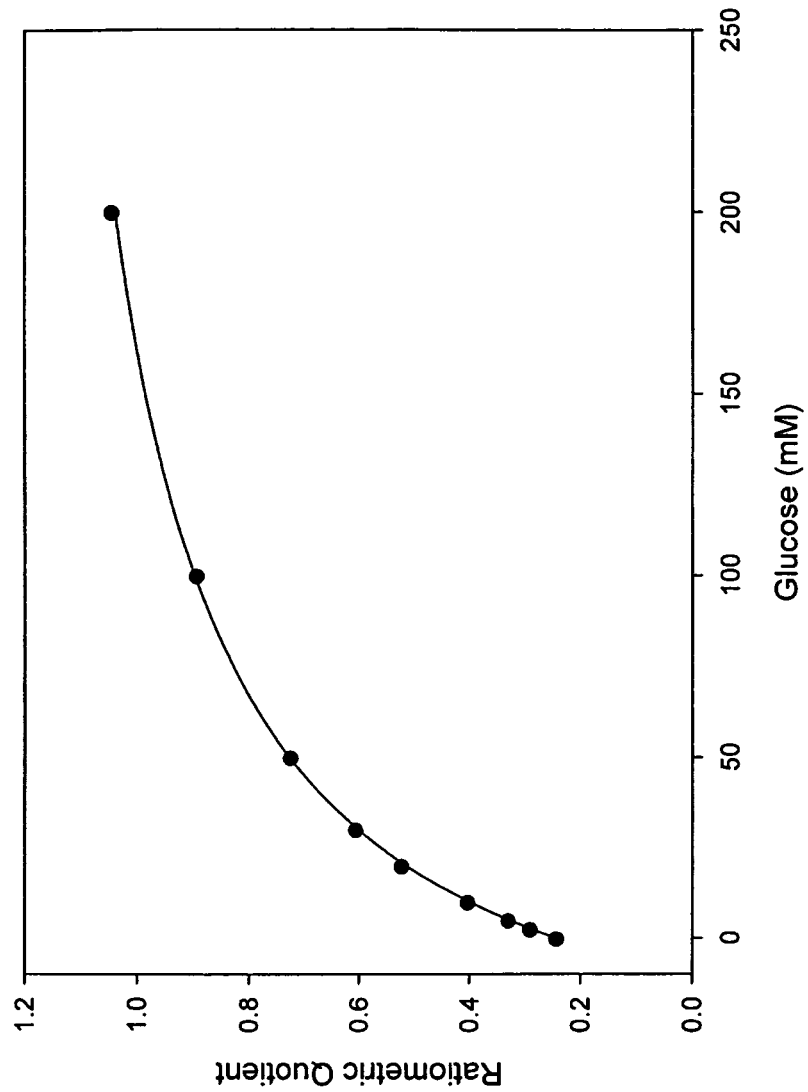
Figure 12:
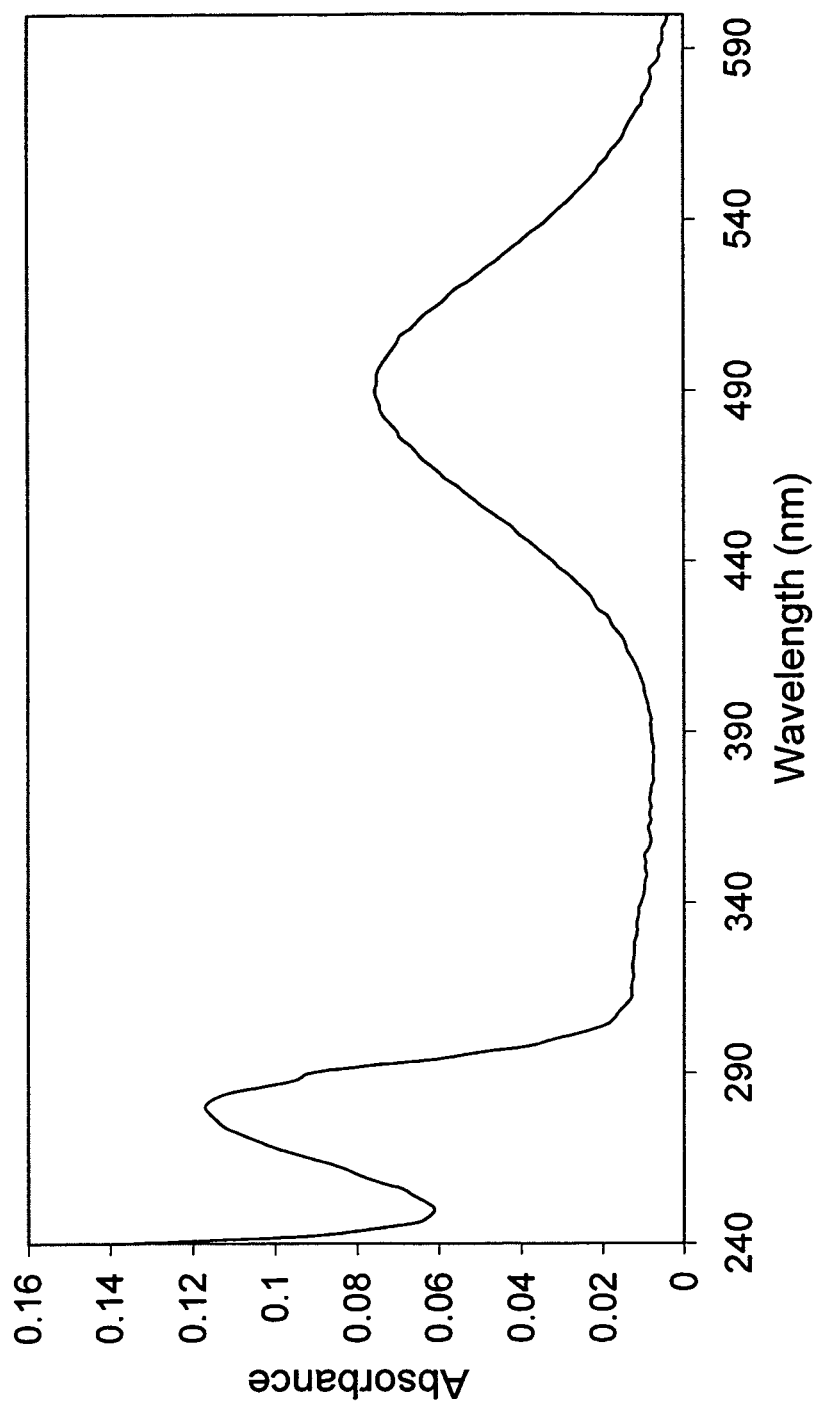
Figure 13A:
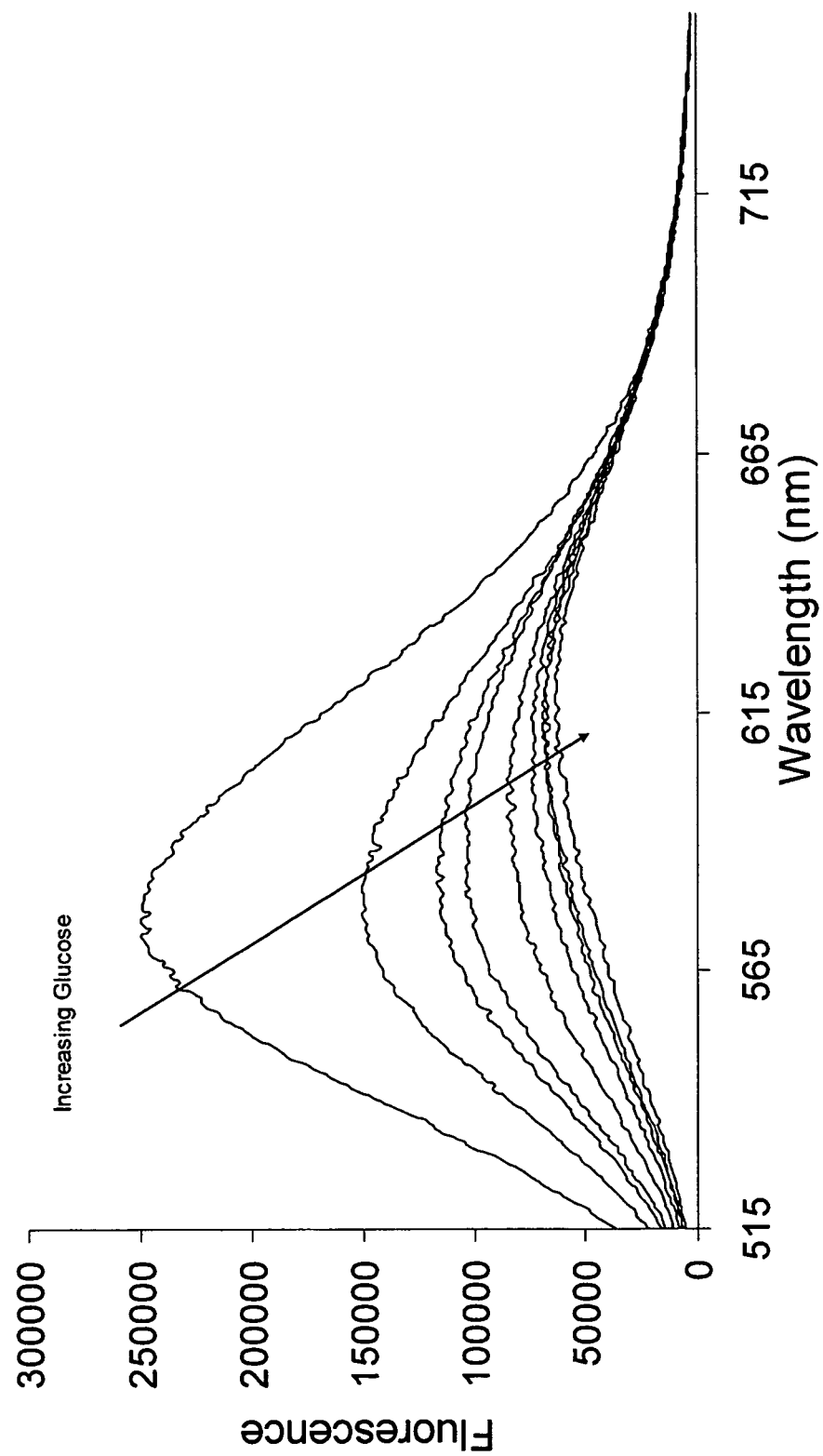
Figure 13B:
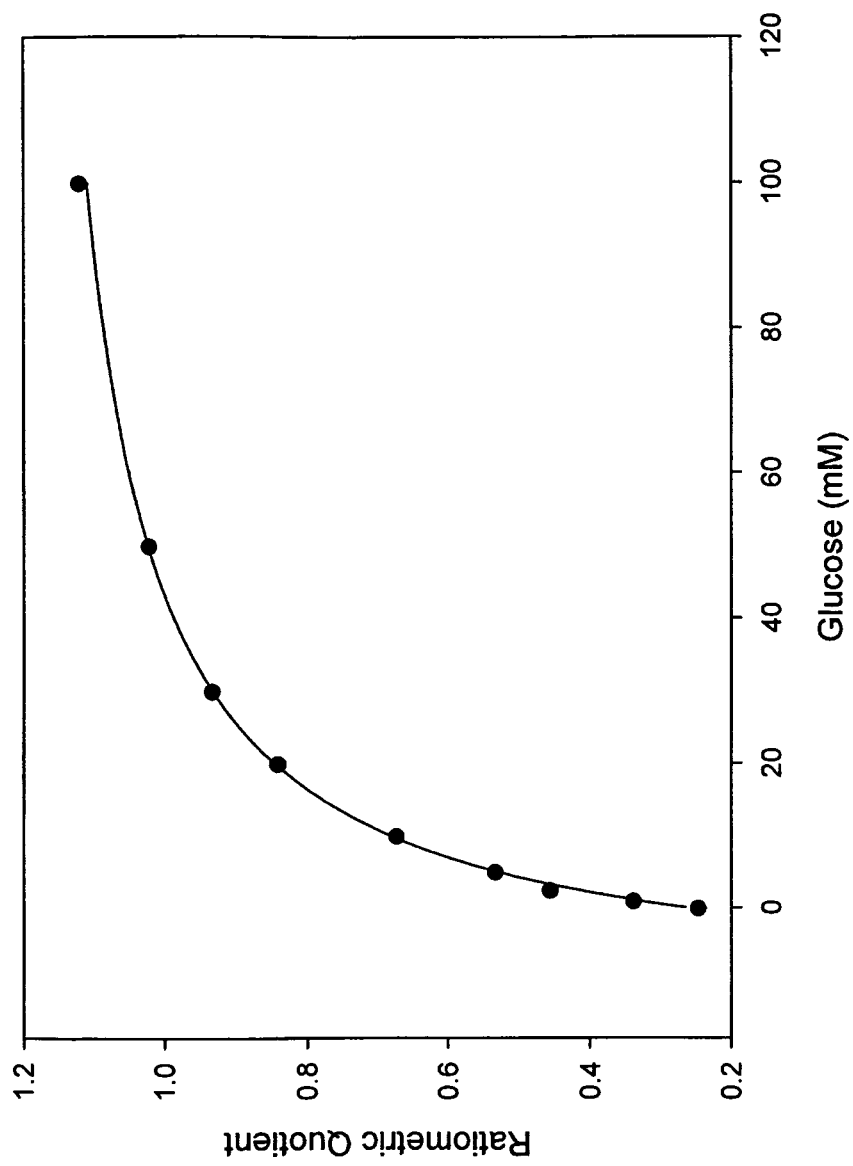
Figure 14:
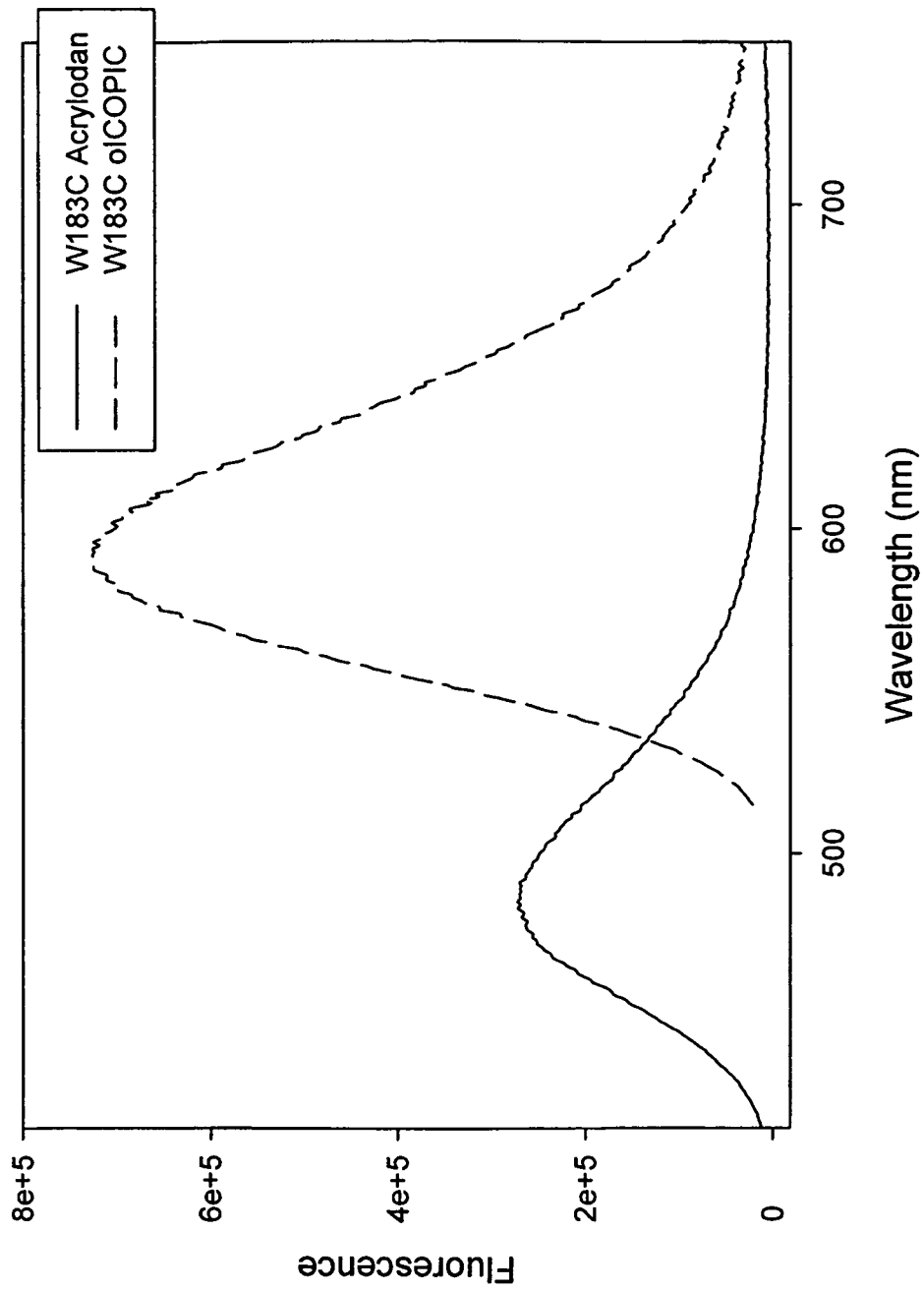

Having thus described the presently disclosed subject matter in general terms, reference will now be made to the accompanying Drawings, which are not necessarily drawn to scale, and wherein:

FIGS. 1A and 1B show the ratiometric response of a presently disclosed fluorophore-binding protein conjugate, e.g., W183-labeled ICOPIC conjugate, to the presence of glucose. FIG. 1A (upper curve) shows the fluorescence intensity of W183-labeled ICOPIC conjugate in the absence of glucose. FIG. 1B (lower curve) shows the fluorescence intensity of W183C-labeled ICOPIC conjugate in the presence of 100 mM glucose;

FIGS. 2A and 2B show representative absorption spectra of a presently disclosed fluorophore-binding protein conjugate, e.g., W183C-labeled ICOPIC conjugate. FIG. 2A shows an absorption spectrum where the conjugates were kept at 4° C. for 3 days. FIG. 2B shows an absorption spectrum where the conjugates were kept at 37° C. for 3 days;

FIGS. 3A and 3B show fluorescence spectra of a presently disclosed ortho-substituted fluorophore-binding pair conjugate, e.g., a SM4-o-ICOPIC ester dye. FIG. 3A shows the fluorescence spectrum of a SM4-o-ICOPIC ester dye in the absence of glucose. FIG. 3B shows the fluorescence spectrum of a SM4-o-ICOPIC ester dye in the presence of glucose;

FIGS. 4A-4C show the stability of a presently disclosed p-ICOPIC dye as monitored by NMR spectrometry. FIG. 4A shows an NMR spectrum of the presently disclosed p-ICOPIC dye at day 1. FIG. 4B shows an NMR spectrum of the presently disclosed p-ICOPIC dye after 7 days at 37° C. FIG. 4C shows an NMR spectrum of the presently disclosed p-ICOPIC dye after 7 days at 55° C.;

FIGS. 5A-5C show the stability of a presently disclosed o-ICOPIC dye as monitored by NMR spectrometry. FIG. 5A shows an NMR spectrum of the presently disclosed o-ICOPIC dye at day 1. FIG. 5B shows an NMR spectrum of the presently disclosed o-ICOPIC dye after 7 days at 37° C. FIG. 5C shows an NMR spectrum of the presently disclosed o-ICOPIC dye after 7 days at 55° C.;

FIGS. 6A and 6B show the stability of a presently disclosed p-ICOPIC dye as monitored by HPLC. FIG. 6A shows an HPLC trace (λ=500 nm) of the presently disclosed p-ICOPIC dye freshly prepared. FIG. 6B shows an HPLC trace (λ=500 nm) of the presently disclosed p-ICOPIC dye at day 14 after incubation;

FIGS. 7A and 7B show the stability of a presently disclosed o-ICOPIC dye as monitored by HPLC. FIG. 7A shows an HPLC trace (λ=500 nm) of the presently disclosed o-ICOPIC dye freshly prepared. FIG. 7B shows an HPLC trace (λ=500 nm) of the presently disclosed o-ICOPIC dye at day 14 after incubation;

FIG. 8 shows the UV-VIS spectrum of an SM4-o-ICOPIC conjugate;

FIGS. 9A and 9B show fluorescence spectra and a binding curve for a SM4-o-ICOPIC conjugate. FIG. 9A shows fluorescence spectra of a SM4-o-ICOPIC conjugate at increasing concentrations of glucose from about 0 mM (upper most curve) to about 200 mM (bottom curve). FIG. 9B shows a binding curve of SM4-o-ICOPIC with glucose;

FIG. 10 shows a UV-VIS spectrum of a presently disclosed W183C-o-ICOPIC conjugate;

FIGS. 11A and 11B show fluorescence spectra and a binding curve for a W183C-o-ICOPIC conjugate. FIG. 11A shows fluorescence spectra of a W183C-o-ICOPIC conjugate at increasing concentrations of glucose from about 0 mM (upper most curve) to about 200 mM (bottom curve). FIG. 11B shows a binding curve of W183C-o-ICOPIC with glucose;

FIG. 12 shows a UV-VIS spectrum of a presently disclosed Y10C-p-ICOPIC conjugate;

FIGS. 13A and 13B show fluorescence spectra and a binding curve for a Y10C-o-ICOPIC conjugate. FIG. 13A shows fluorescence spectra of a Y10C-o-ICOPIC conjugate at increasing concentrations of glucose from about 0 mM (upper most curve) to about 200 mM (bottom curve). FIG. 13B shows a binding curve of Y10-o-ICOPIC with glucose; and FIG. 14 shows the fluorescence spectra of W183C-o-ICOPIC (dashed line) and W183C-acrylodan (solid line).

DETAILED DESCRIPTION

The presently disclosed subject matter now will be described more fully hereinafter with reference to the accompanying Drawings, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Following long-standing patent law convention, the terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

I. Environmentally Sensitive Fluorescent Dyes and Methods of Use Thereof

The presently disclosed subject matter provides thiol-reactive, environmentally sensitive fluorescent dyes, also referred to herein as fluorophores, which have an emission wavelength in the visible spectral region and exhibit a ratiometric response to one or more ligands or target analytes. As used herein, the term "fluorophore" is meant to include a moiety of a larger molecule or conjugate that can be induced to emit fluorescence when irradiated, i.e., excited, by electromagnetic radiation of an appropriate wavelength. More particularly, a fluorophore can be a functional group of a molecule or conjugate that absorbs light of a certain wavelength and emits light at different wavelength. The intensity and the wavelength of the light emitted, as well as other fluorescence properties including, but not limited to, fluorescence lifetime, anisotropy, polarization, and combinations thereof, depend on the identity of the fluorophore and its chemical environment. A fluorophore can include a fluorescent molecule, such as the presently disclosed fluorescent dyes.

A. Fluorescent Dyes Having a Thiol-Reactive Group

In some embodiments, the presently disclosed subject matter provides a fluorophore having the formula:

A-Y wherein:

A is selected from the group consisting of a coumarin nucleus and an aza-coumarin nucleus;

Y is selected from the group consisting of:

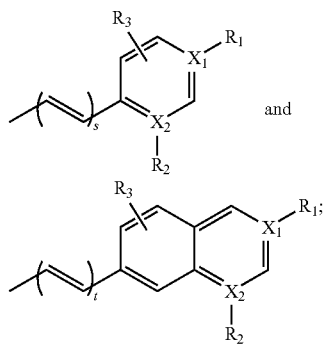

wherein:

s and t are each independently an integer from 1 to 8;

each $X_1$ and $X_2$ is independently selected from the group consisting of C, S, and N, wherein at least one of $X_1$ and $X_2$ is N, under the proviso that (i) when $X_1$ is C or S, $R_1$ is Z, or when $X_2$ is C or S, $R_2$ is Z, as Z is defined herein below; (ii) if both $X_1$ and $X_2$ are N at the same time, at least one of $R_1$ and $R_2$ is absent; and (iii) when $X_1$ is N, $R_1$ when present is Z', or when $X_2$ is N, $R_2$ when present is Z', wherein Z' is selected from the group consisting of:

—$(CH_2)_nX_3C(\!=\!\!O)$—$R_4$,

-continued

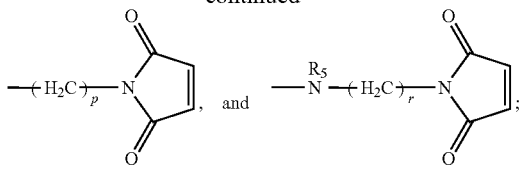

wherein:

n, p, and r are each independently an integer from 1 to 8;

$X_3$ is O or $NR_6$;

each $R_3$, $R_5$, $R_6$ and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

$R_4$ is —$(CH_2)_m$—$X_4$;

wherein m is an integer from 1 to 8; and $X_4$ is halogen.

In the embodiments disclosed immediately hereinabove, wherein at least one of $X_1$ and $X_2$ are N and at least one of $R_1$ and $R_2$ are present and bound to a nitrogen atom, the nitrogen atom having $R_1$ or $R_2$ bound thereto is a quaternary nitrogen atom, i.e., a pentavalent nitrogen atom bound to four carbon atoms and having a positive charge available for binding ionically to an anion for the remaining valence.

In some embodiments, the presently disclosed fluorophores include a coumarin nucleus or a derivative of a coumarin nucleus. Suitable nuclei are described in U.S. Patent Application Publication No. 2006/0280652, filed May 18, 2005, which is incorporated by reference in its entirety. As used herein, a "derivative of a coumarin nucleus" refers to a chemical compound that is derived from or obtained from a parent compound, e.g., coumarin, and contains essential elements of the parent compound but typically has one or more different functional groups. Such functional groups can be added to a parent compound, for example, to improve the molecule's solubility, absorption, biological half life, fluorescent properties, and the like, or to decrease the toxicity of the molecule, eliminate or attenuate any undesirable side effect of the molecule, and the like. A derivative of a coumarin nucleus is meant to include any chemical modification, addition, deletion, or substitution to a coumarin nucleus. Further, a derivative of a coumarin nucleus can include any reaction product of the derivative, for example, the reaction product of the derivative with an amino acid residue. Accordingly, in some embodiments, the presently disclosed fluorophore can include a coumarin nucleus having a reactive group that can be conjugated, e.g., covalently attached, to an amino acid, for example, an amino acid residue of a protein. A non-limiting example of a derivative is an ester or amide of a parent compound having a carboxylic acid functional group.

More particularly, in some embodiments, the coumarin nucleus can include a thiol-reactive group that can be conjugated to the thiol moiety of a cysteine amino acid residue in a natural or an engineered or mutated protein. As used herein, the term "thiol-reactive group" refers to a substituent group that can react with a thiol moiety to form a carbon-sulfur bond. Examples of suitable thiol-reactive groups that can be introduced into the presently disclosed fluorophores include a halo-acetyl group and a halo-acetamide group. In some embodiments, the halo-acetyl group includes an iodoacetyl group, whereas the halo-acetamide group can include an iodoacetamide or bromoacetamide group. One of ordinary skill in the art upon review of the presently disclosed subject matter would recognize that other thiol-reactive groups known in the art, such as maleimide groups, are suitable for use with the presently disclosed subject matter.

Thus, in some embodiments of the fluorophore of formula A-Y, A is coumarin and the presently disclosed fluorophore has the following formula:

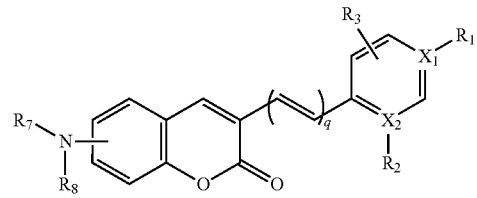

wherein:

q is an integer from 1 to 8;

each $X_1$ and $X_2$ is independently selected from the group consisting of C, S, and N, wherein at least one of $X_1$ and $X_2$ is N, under the proviso that (i) when $X_1$ is C or S, $R_1$ is Z, or when $X_2$ is C or S, $R_2$ is Z, as Z is defined herein below; (ii) if both $X_1$ and $X_2$ are N at the same time, at least one of $R_1$ and $R_2$ is absent; and (iii) when $X_1$ is N, $R_1$ when present is Z', or when $X_2$ is N, $R_2$ when present is Z', wherein Z' is selected from the group consisting of:

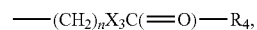

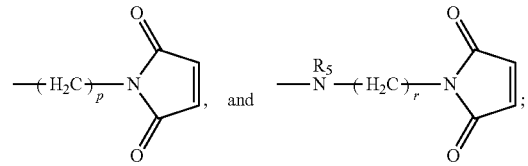

wherein:

n, p, and r are each independently an integer from 1 to 8;

$X_3$ is O or $NR_6$;

each $R_3$, $R_5$, $R_6$, $R_7$, $R_8$, and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_7$ and $R_8$ together represent a $C_2$ to $C_{10}$ alkyl, $C_2$ to $C_{10}$ substituted alkyl, or $C_2$ to $C_{10}$ alkylene;

$R_4$ is —$(CH_2)_m$—$X_4$;

wherein m is an integer from 1 to 8; and $X_4$ is halogen.

In some embodiments, the fluorophore of formula A-Y is selected from the group consisting of:

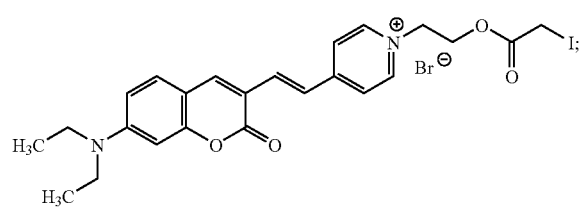

-continued

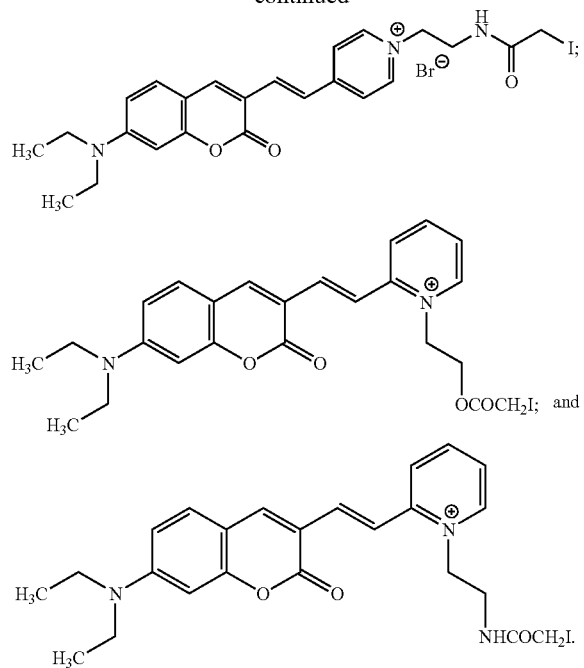

As described immediately herein below, the presently disclosed fluorophores of formula A-Y can be conjugated with a binding member of a specific binding pair, such as a binding protein, to form a biosensor compound that can be used to detect one or more analytes in a sample under test.

B. Biosensor Compounds Comprising Environmentally-Sensitive Fluorescent Dyes Having a Thiol-Reactive Group The presently disclosed fluorophores can be used in combination with binding protein assays to detect physiologically important molecules, including metabolites, such as glucose, fatty acids, and lactates, in biological samples. In some embodiments, the presently disclosed fluorophores include a reactive group that can be used to couple or conjugate the fluorophore with another molecule, including a member of a specific binding pair, such as a binding protein or a receptor, which has an affinity for a specific ligand or analyte.

As used herein, the term "conjugate" refers to a molecule comprising two or more subunits bound together, optionally through a linking group, to form a single molecular structure. The binding can be made either by a direct chemical bond between the subunits or through a linking group. Such binding in a conjugate typically is irreversible. As used herein, the term "affinity" refers to the strength of the attraction between one binding member of a specific binding pair to another binding member of a specific binding pair at a particular binding site. The term "specificity" and derivations thereof, refer to the likelihood that a binding member will bind to another member of a specific binding pair. Such binding between one binding member, e.g., a binding protein, to another binding member of a specific binding pair, e.g., a ligand or analyte, can be reversible.

When bound to a target analyte or ligand, the presently disclosed conjugates can exhibit a detectable change in a fluorescence property in response to changes in the environment of the binding protein or receptor of the fluorophore conjugate. The detectable change in the fluorescent property can include a shift in the fluorescence emission wavelength, a change in fluorescence intensity, a change in fluorescence lifetime, a change in anisotropy, a change in polarization, and combinations thereof.

Without wishing to be bound to any one particular theory, the binding protein or receptor can adopt two conformations: a ligand-free open form and a closed form when bound to a ligand. These two conformations interconvert, for example, via a global hinge-binding mechanism upon ligand binding or changes in ligand concentration. By positioning environmentally-sensitive fluorophores in locations that undergo local conformational changes in concert with these global conformational changes, such ligand-mediated conformational changes can be exploited to couple ligand binding to changes in one or more fluorescence properties. Accordingly, these engineered conformational coupling mechanisms enable reagentless optical biosensors to be formed from selected binding proteins and environmentally-sensitive fluorophores.

As used herein, the terms "biosensor" and "biosensor compound" generally refer to a compound that undergoes a detectable change in specific response to a ligand or target analyte. More particularly, the presently disclosed biosensors combine the molecular recognition properties of biological macromolecules, such as a binding protein, with environmentally-sensitive fluorophores that produce a detectable change in a fluorescent property upon ligand binding. Accordingly, a biosensor translates a binding event into a directly measurable fluorescent property.

In some embodiments, the presently disclosed subject matter provides a biosensor compound having the formula:

A-Y'—B wherein:

A is selected from the group consisting of a coumarin nucleus and an aza-coumarin nucleus;

Y' is selected from the group consisting of:

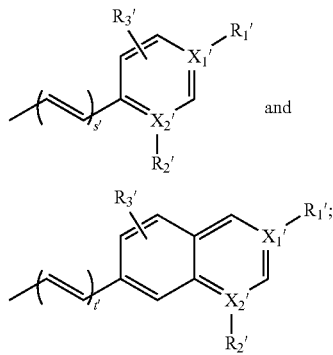

wherein:

s' and t' are each independently an integer from 1 to 8;

each $X_1'$ and $X_2'$ is independently selected from the group consisting of C, S, and N, wherein at least one of $X_1'$ and $X_2'$ is N, under the proviso that (i) when $X_1'$ is C or S, $R_1'$ is Z, or when $X_2'$ is C or S, $R_2'$ is Z, as Z is defined herein below; (ii) if both $X_1'$ and $X_2'$ are N at the same time, at least one of $R_1'$ and $R_2'$ is absent; and (iii) when $X_1'$ is N, $R_1'$ when present is Z', or when $X_2'$ is N, $R_2'$ when present is Z", wherein Z" is selected from the group consisting of:

—$(CH_2)_xX_3'C(=O)$—$R_4'$,

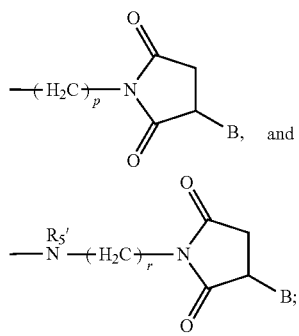

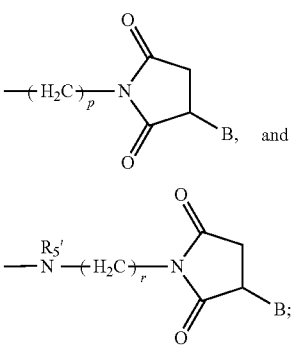

wherein, n, p, and r are each independently an integer from 1 to 8;

$X_3'$ is O or $NR_6'$;

each $R_3'$, $R_5'$, $R_6'$ and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

$R_4'$ is —$(CH_2)_m$—B;

wherein m is an integer from 1 to 8; and

B is a binding member having a binding affinity for a ligand or analyte to be detected; and wherein the biosensor compound exhibits a detectable change in a fluorescence property as a result of binding to the ligand or analyte or as a result of a change in concentration of the ligand or analyte in a sample under test.

In some embodiments, of the presently disclosed biosensor compound, A is coumarin and the biosensor compound of formula A-Y'—B has the following formula:

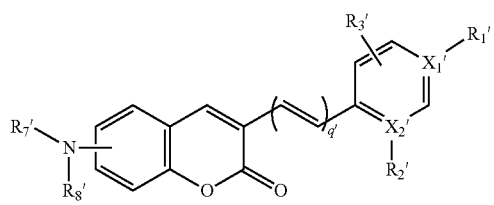

wherein:

q' is an integer from 1 to 8;

each $X_1'$ and $X_2'$ is independently selected from the group consisting of C, S, and N, wherein at least one of $X_1'$ and $X_2'$ is N, under the proviso that (i) when $X_1'$ is C or S, $R_1'$ is Z, or when $X_2'$ is C or S, $R_2'$ is Z, as Z is defined herein below; (ii) if both $X_1'$ and $X_2'$ are N at the same time, at least one of $R_1'$ and $R_2'$ is absent; and (iii) when $X_1'$ is N, $R_1'$ when present is Z'', or when $X_2'$ is N, $R_2'$ when present is Z'', wherein Z'' is selected from the group consisting of:

—$(CH_2)_{n'}X_3'C(=O)$—$R_4'$, wherein:

n, p, and r are each independently an integer from 1 to 8;

$X_3'$ is O or $NR_6'$;

each $R_3'$, $R_5'$, $R_6'$, $R_7'$, $R_8'$, and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_7'$ and $R_8'$ together represent a $C_2$ to $C_{10}$ alkyl, $C_2$ to $C_{10}$ substituted alkyl, or $C_2$ to $C_{10}$ alkylene;

$R_4'$ is —$(CH_2)_{m'}$—$X_4'$;

wherein m' is an integer from 1 to 8; and

B is a binding member having a binding affinity for a ligand or analyte to be detected.

In some embodiments, the biosensor compound is selected from the group consisting of:

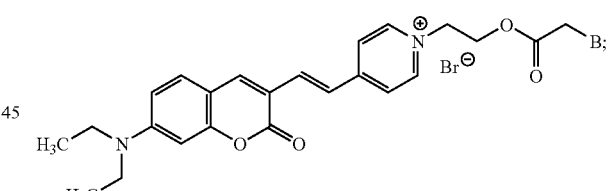

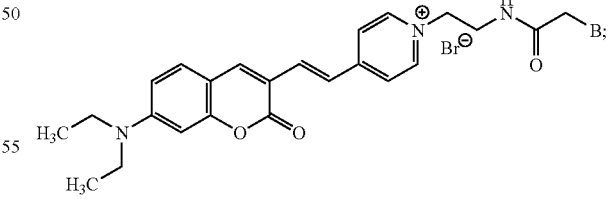

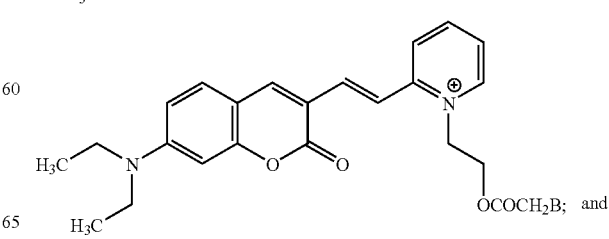

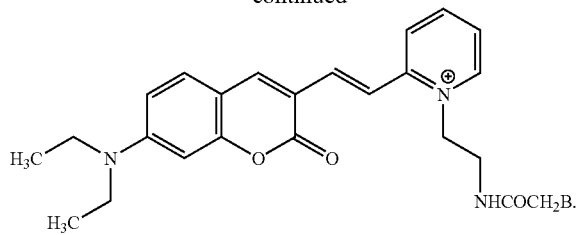

In some embodiments, the binding member B is a binding protein. As used herein, the term "binding protein" refers to a protein, that when conjugated with a fluorophore, interacts with a specific analyte or ligand in a manner capable of producing a detectable florescence signal differentiable from when a target analyte or ligand is present or absent, or when a target analyte or ligand is present in varying concentrations over time. The term "producing a detectable signal" refers to the ability to recognize a change in a property of a reporter group, e.g., a fluorophore, in a manner that enables the detection of ligand-protein binding. Further, the producing of a detectable signal can be reversible or non-reversible. The signal-producing event includes continuous, programmed, and episodic means, including one-time or reusable applications. The reversible signal-producing event can be instantaneous or can be time-dependent, so long as a correlation with the presence or concentration of analyte is established.

In some embodiments, the binding member conjugated with the presently disclosed fluorophores comprises a polypeptide or protein. In some embodiments, the binding protein is selected from the group consisting of W183C, SM4, and Y10C. Representative binding proteins suitable for use with the presently disclosed fluorophores, include, but are not limited to periplasmic binding proteins (PBPs). As used herein a PBP is a protein characterized by its three-dimensional configuration (tertiary structure), rather than its amino acid sequence (primary structure) and is characterized by a lobe-hinge-lobe region. The PBP normally binds an analyte specifically in a cleft region between the lobes of the PBP. Further, the binding of an analyte in the cleft region can cause a conformational change to the PBP that makes detection of the analyte possible. Periplasmic binding proteins suitable for use with the presently disclosed fluorophores include any protein that possesses the structural characteristics described herein. Analyzing the three-dimensional structure of a protein to determine the characteristic lobe-hinge-lobe structure of the PBPs is well within the capabilities of one of ordinary skill in the art. Examples of PBPs include, but are not limited to, glucose-galactose binding protein (GGBP), maltose binding protein (MBP), ribose binding protein (RBP), arabinose binding protein (ABP), dipeptide binding protein (DPBP), glutamate binding protein (GluBP), iron binding protein (FeBP), histidine binding protein (HBP), phosphate binding protein (PhosBP), glutamine binding protein (QBP), oligopeptide binding protein (OppA), or derivatives thereof, as well as other proteins that belong to the families of proteins known as periplasmic binding protein like I (PBP-like I) and periplasmic binding protein like II (PBP-like II). The PBP-like I and PBP-like II proteins have two similar lobe domains comprised of parallel β-sheets and adjacent α helices. The glucose-galactose binding protein (GGBP) belongs to the PBP-like I family of proteins, whereas the maltose binding protein (MBP) belongs to the PBP-like II family of proteins. The ribose binding protein (RBP) is also a member of the PBP family of proteins. Other non-limiting examples of periplasmic binding proteins are listed in Table I.

TABLE I

Genes Encoding Common Periplasmic Binding Proteins.

| Gene name | Substrate | Species |
|---|---|---|
| alsB | Allose | E. coli |
| araF | Arabinose | E. coli |
| AraS | Arabinose/fructose/xylose | S. solfataricus |
| argT | Lysine/arginine/ornithine | Salmonella typhimurium |
| ArtI | Arginine | E. coli |
| artJ | Arginine | E. coli |
| b1310 | Unknown (putative, multiple sugar) | E. coli |
| b1487 | Unknown (putative, oligopeptide binding) | E. coli |
| b1516 | Unknown (sugar binding protein homolog) | E. coli |
| butE | vitamin B12 | E. coli |
| CAC1474 | Proline/glycine/betaine | Clostridium acetobutylicum |
| Cbt | Dicarboxylate (Succinate, malate, fumarate) | E. coli |
| CbtA | Cellobiose | S. solfataricus |
| chvE | Sugar | A. tumefaciens |
| CysP | Thiosulfate | E. coli |
| dctP | C4-dicarboxylate | Rhodobacter capsulatus |
| dppA | Dipeptide | E. coli |
| FbpA | Iron | Neisseria gonorrhoeae |
| fecB | Fe(III)-dicitrate | E. coli |
| fepB | enterobactin-Fe | E. coli |
| fhuD | Ferrichydroxamate | E. coli |
| FliY | Cystine | E. coli |
| GlcS | glucose/galactose/mannose | S. solfataricus |
| glnH (protein: GLNBP) | Gluconate | E. coli |
| gntX | Gluconate | E. coli |
| hemT | Haemin | Y. enterocolitica |
| HisJ (protein: HBP) | Histidine | E. coli |
| hitA | Iron | Haemophilus influenzae |
| livJ | Leucine/valine/isoleucine | E. coli |
| livK (protein: L-BP) | Leucine | E. coli |
| malE (protein: MBP) | maltodextrin/maltose | E. coli |
| mglB | glucose/galactose (protein: GGBP) | E. coli |
| modA | Molybdate | E. coli |
| MppA | L-alanyl-gamma-D-glutamyl-meso-diaminopimelate | E. coli |
| nasF | nitrate/nitrite | Klebsiella oxytoca |
| nikA | Nickel | E. coli |
| opBC | Choline | B. subtilis |
| OppA | Oligopeptide | Salmonella typhimurium |
| PhnD | Alkylphosphonate | E. coli |
| PhoS (Psts) | Phosphate | E. coli |
| potD | putrescine/spermidine | E. coli |
| potF | Polyamines | E. coli |
| proX | Betaine | E. coli |
| rbsB | Ribose | E. coli |
| SapA | Peptides | S. typhimurium |
| Sbp | Sulfate | Salmonella typhimurium |
| TauA | Taurin | E. coli |
| TbpA | Thiamin | E. coli |
| tctC | Tricarboxylate | Salmonella typhimurium |
| TreS | Trehalose | S. solfataricus |
| tTroA | Zinc | Treponema pallidum |
| UgpB | sn-glycerol-3-phosphate | E. coli |
| XylF | Xylose | E. coli |

TABLE I-continued

Genes Encoding Common Periplasmic Binding Proteins.

| Gene name | Substrate | Species |
|---|---|---|
| YaeC | Unknown (putative) | E. coli |
| YbeJ (GltI) | glutamate/aspartate (putative, superfamily: lysine-arginine-ornithine-binding protein) | E. coli |
| YdcS (b1440) | Unknown (putative, spermidine) | E. coli |
| YehZ | Unknown (putative) | E. coli |
| YejA | Unknown (putative, homology to periplasmic oligopeptide-binding protein-*Helicobactr pylori*) | E. coli |
| YgiS (b3020) | Oligopeptides (putative) | E. coli |
| YhbN | Unknown | E. coli |
| YhdW | Unknown (putative, amino acids) | E. coli |
| YliB (b0830) | Unknown (putative peptides) | E. coli |
| YphF | Unknown (putative sugars) | E. coli |
| Ytrf | Acetoin | B. subtilis |

Other examples of proteins that can comprise the binding members include, but are not limited to intestinal fatty acid binding proteins (FAPBs). The FABPs are a family of proteins that are expressed at least in the liver, intestine, kidney, lungs, heart, skeletal muscle, adipose tissue, abnormal skin, adipose, endothelial cells, mammary gland, brain, stomach, tongue, placenta, testis, retina. The family of FABPs is, generally speaking, a family of small intracellular proteins (about 14 kDa) that bind fatty acids and other hydrophobic ligands through non-covalent interactions. See Smith, E. R. and Storch, J., *J. Biol. Chem.*, 274 (50):35325-35330 (1999), which is incorporated herein by reference in its entirety. Members of the FABP family of proteins include, but are not limited to, proteins encoded by the genes FABP1, FABP2, FABP3, FABP4, FABP5, FABP6, FABP7, FABP (9) and MP2. Proteins belonging to the FABP include I-FABP, L-FABP, H-FABP, A-FABP, KLBP, mal-1, E-FABP, PA-FABP, C-FABP, S-FABP, LE-LBP, DA11, LP2, Melanogenic Inhibitor, and the like.

In some embodiments, the binding member is selected from the group consisting of a GGBP, a FABP and a GGBP derivative. In one embodiment of the presently disclosed subject matter, a mutated glucose/galactose binding protein (GGBP) comprises a detectable reporter group, e.g., a coumarin-based fluorophore, whose detectable characteristics alter upon glucose binding. The change in the detectable characteristics can be due to an alteration in the environment of the fluorophore attached to the mutated GGBP or to a conformational change of the protein resulting from binding. In some embodiments, the FABP is I-FABP.

As used herein, a "derivative of a protein" or "a derivative of a polypeptide" is a protein or polypeptide that shares substantial sequence identity with the wild-type protein. Derivative proteins or polypeptides of the presently disclosed subject matter can be made or prepared by techniques well known to those of skill in the art. Examples of such techniques include, but are not limited to, mutagenesis and direct synthesis. Derivative proteins also can be modified, either by natural processes, such as post-translational processing, or by chemical modification techniques which are well known in the art. Such modifications are well described in basic texts and in more detailed monographs, as well as in voluminous research literature. Modifications can occur anywhere in the polypeptide chain, including the peptide backbone, the amino acid side-chains and the amino or carboxyl termini. It will be appreciated that the same type of modification can be present in the same or varying degrees at several sites in a given polypeptide or protein. Also, a given polypeptide or protein can contain more than one modification. Examples of modifications include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Polypeptides or proteins can even be branched as a result of ubiquitination, and they can be cyclic, with or without branching. (See, e.g., T E. Creighton, *Proteins—Structure And Molecular Properties,* 2nd ed., W.H. Freeman and Company, New York (1993); Wold, F., "Posttranslational Protein Modifications: Perspectives and Prospects," in *Posttranslational Covalent Modification Of Proteins*, B. C. Johnson, Ed., Academic Press, New York (1983); Seifter et al., *Methods in Enzymol,* 182:626-646 (1990) and Rattan et al., *Ann NY Acad Sci.,* 663:48-62 (1992), each of which is incorporated herein by reference. Examples of derivative proteins include, but are not limited to, mutant and fusion proteins.

A "mutant protein" is used herein as it is known in the art. In general, a mutant protein can be created by addition, deletion or substitution of the wild-type primary structure of the protein or polypeptide. Mutations include, for example, the addition or substitution of cysteine groups, non-naturally occurring amino acids, and replacement of substantially non-reactive amino acids with reactive amino acids. A mutant protein can be mutated to bind more than one analyte in a specific manner. Indeed, the mutant proteins can possess specificity towards its wild-type analyte and another target ligand. Likewise, a mutant protein can be able to only bind an analyte or analytes that the wild-type binding protein does not bind. Methods of generating mutant proteins are well-known in the art. For example, Looger, L. L. et al., Nature 423 (6936): 185-190 (2003), which is incorporated herein by reference, disclose methods for redesigning binding sites within periplasmic binding proteins that provide new analyte-binding properties for the proteins. These mutant binding proteins retain the ability to undergo conformational change, which can produce a directly generated signal upon analyte-binding. By introducing between 5 and 17 amino acid changes, Looger, et al. constructed several mutant proteins, each with new selectivities for TNT (trinitrotoluene), L-lactate, or serotonin. For example, Looger et al. generated L-lactate binding proteins from ABP, GGBP, RBP, HBP and QBP.

Table II lists other mutations to GGBP and is taken from Looger L. L. et al., Nature 423: 185-190, (2003), which is incorporated herein by reference in its entirety.

TABLE II

Mutations of GGBP residues providing L-lactate selectivity.

| Residue: | 10 | 14 | 16 | 91 | 92 | 152 | 154 | 158 | 183 | 236 | 256 |
|---|---|---|---|---|---|---|---|---|---|---|---|
| Wildtype GGBP | Y | D | F | N | K | H | D | R | W | D | N |
| Lactate-specific mutant G1 | K | K | F | K | L | M | H | K | K | A | D |
| Lactate-specific mutant G2 | K | M | K | K | L | K | K | M | K | A | S |

Examples of mutations of a GGBP protein, for example the GGBP protein of GenBank Accession No. PO2927 without the 23 amino acid leader sequence (i.e., the mature chain), include, but are not limited to, having a cysteine substituted for lysine at position 11 (K11C), a cysteine substituted for aspartic acid at position 14 (D14C), a cysteine substituted for valine at position 19 (V19C), a cysteine substituted for asparagine at position 43 (N43C), a cysteine substituted for glycine at position 74 (G74C), a cysteine substituted for tyrosine at position 107 (Y107C), a cysteine substituted for threonine at position 110 (T110C), a cysteine substituted for serine at position 112 (S112C), a double mutant including a cysteine substituted for serine at position 112 and serine substituted for leucine at position 238 (S112C/L238S), a cysteine substituted for lysine at position 113 (K113C), a cysteine substituted for lysine at position 137 (K137C), a cysteine substituted for glutamic acid at position 149 (E149C), a double mutant including a cysteine substituted for glutamic acid at position 149 and an arginine substituted for alanine at position 213 (E149C/A213R), a double mutant including a cysteine substituted for glutamic acid at position 149 and a serine substituted for leucine at position 238 (E149C/L238S), a double mutant including a serine substituted for alanine at position 213 and a cysteine substituted for histidine at position 152 (H152C/A213S), a cysteine substituted for methionine at position 182 (M182C), a cysteine substituted for alanine at position 213 (A213C), a double mutant including a cysteine substituted for alanine at position 213 and a cysteine substituted for leucine at position 238 (A213C/L238C), a cysteine substituted for methionine at position 216 (M216C), a cysteine substituted for aspartic acid at position 236 (D236C), a cysteine substituted for leucine at position 238 (L238C) a cysteine substituted for aspartic acid at position 287 (D287C), a cysteine substituted for arginine at position 292 (R292C), a cysteine substituted for valine at position 296 (V296C), a triple mutant including a cysteine substituted for glutamic acid at position 149 and a serine substituted for alanine at position 213 and a serine substituted for leucine at position 238 (E149C/A213S/L238S), a triple mutant including a cysteine substituted for glutamic acid at position 149 and an arginine substituted for alanine at position 213 and a serine substituted for leucine at position 238 (E149C/A213R/L238S), a cysteine substituted for glutamic acid at position 149 and a cysteine substituted for alanine at position 213 and a serine substituted for leucine at position 238 (E149C/A213C/L238S).

The mutation can serve one or more of several purposes. For example, a naturally occurring protein can be mutated to change the long-term stability, including thermal stability, of the protein, to conjugate the protein to a particular encapsulation matrix or polymer, to provide binding sites for detectable reporter groups, to adjust its binding constant with respect to a particular analyte, or combinations thereof.

The analyte and mutated protein can act as binding partners. The term "associates" or "binds" as used herein refers to binding partners having a relative binding constant (Kd) sufficiently strong to allow detection of binding to the protein by a detection means. The Kd can be calculated as the concentration of free analyte at which half the protein is bound, or vice versa. When the analyte of interest is glucose, the Kd values for the binding partners are between about 0.0001 mM and about 50 mM.

In addition to changing binding characteristics, derivative polypeptides or proteins also can be used to incorporate a presently disclosed fluorophore onto or within the binding member. The fluorophores can be used to indicate a change in the binding member, including, but not limited to, three-dimensional conformational changes, changes in orientation of the amino acid side chains of proteinaceous binding domains, and redox states of the binding member. With the addition/substitution of one or more residues into the primary structure of a protein, some of the labeling moieties used in the current methods and compositions can be attached through chemical means, such as reduction, oxidation, conjugation, and condensation reactions. Examples of residues commonly used to label proteins include, but are not limited to, lysine and cysteine. For example, any thiol-reactive group can be used to attach a fluorophore to a naturally occurring or engineered cysteine in the primary structure of the polypeptide. Also, for example, lysine residues can be labeled using succinimide ester derivatives of fluorophores. See Richieri, G. V. et al., *J. Biol. Chem.*, 267: 23495-501 (1992), which is incorporated herein by reference.

The fluorophore can be attached to the mutated protein, for example a GGBP, by any conventional means known in the art. For example, the reporter group can be attached via amines or carboxyl residues on the protein. Exemplary embodiments include covalent coupling via thiol groups on cysteine residues of the mutated or native protein. For example, for mutated GGBP, cysteines can be located at position 10, at position 11, position 14, at position 15, position 19, at position 26, at position 43, at position 74, at position 92, at position 93, position 107, position 110, position 112, at position 113, at position 137, at position 149, at position 152, at position 154, at position 182, at position 183, at position 186, at position 211, at position 213, at position 216, at position 238, at position 240, at position 242, at position 255, at position 257, at position 287, at position 292, at position 294, and at position 296.

The presently disclosed fluorescent dyes can be covalently attached to a binding protein in a site-specific manner to obtain the desired change in fluorescence. The fluorescent dye can be attached at a site on the binding protein so that the conformational change maximizes the change in fluorescence properties. Conjugates containing fluorophores attached at various sites, for example, cysteine mutant sites constructed in mutated GGBPs, can be screened to identify which sites result in the largest change in fluorescence upon glucose binding.

In some embodiments, the binding member is at least one fragment of a receptor, wherein the receptor is a protein in nature and is capable of binding to a suitable ligand via an active site, and wherein at least one amino acid residue of the fragment is located in the proximity of the active site and is a cysteine residue or is substituted with a cysteine residue, as described in U.S. Patent Application Publication No. 2003/0153012 to Renard et al., which is incorporated herein by reference in its entirety.

As used herein, the term "receptor" refers to a protein macromolecule having an active site capable of binding a ligand. More particularly, a "receptor" refers to an antibody, a hormone or bacterial receptor, an affinity protein, a transport protein, a viral receptor, or any polypeptide having a specific affinity for a ligand.

In some embodiments, the receptor can have one or more disulfide bridges. In some embodiments, the receptor can be an antibody or an antibody fragment, including, but not limited to, an Fv, scFv, or Fab fragment, or a miniantibody. In some embodiments, the antibody can be a natural or artificial monoclonal antibody.

As used herein, the term "ligand" refers to any molecule capable of binding to the receptor via an active site. In some embodiments, the ligand is a protein, a peptide or hapten antigen, such as a bacterial antigen, or a hormone, a cytokine, an interleukin, a tumor necrosis factor (TNF) a growth factor, a viral protein, or a peptide or nucleotide sequence.

As used herein, the term "active site" when referring to, for example, "an active site of the receptor or of the receptor fragment" refers to amino acid residues of the receptor or receptor fragment that contribute to the binding of the ligand. This active site also can be referred to as a "binding site" or "paratope."

The term "proximity" as used herein refers to the position of amino acid residues of the receptor that are in direct contact with the ligand, those that are in contact by water molecules, and those for which the solvent accessible surface area (ASA), as that term in known in the art, see, e.g., Creighton, T. E., "Proteins: Structure and molecular properties," 2nd ed., (W.H. Freeman & Co., New York) 227-229 (1993), is modified by the binding of the ligand.

C. Methods of Detecting the Presence or Amount of a Metabolite

In some embodiments, the presently disclosed subject matter provides a method for determining the presence or amount of one or more analytes in a sample, the method comprising:

(a) providing a biosensor compound having at least one mutated binding protein with a fluorophore covalently attached thereto through a thiol group of the mutated binding protein, wherein the biosensor compound has the following formula:

A-Y'—B wherein:
A is selected from the group consisting of a coumarin nucleus and an aza-coumarin nucleus;
Y' is selected from the group consisting of:

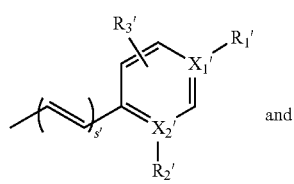

and

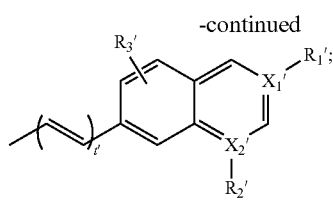

wherein
s' and t' are each independently an integer from 1 to 8;
each $X_1'$ and $X_2'$ is independently selected from the group consisting of C, S, and N, wherein at least one of $X_1'$ and $X_2'$ is N, under the proviso that (i) when $X_1'$ is C or S, $R_1'$ is Z, or when $X_2'$ is C or S, $R_2'$ is Z, as Z is defined herein below; (ii) if both $X_1'$ and $X_2'$ are N at the same time, at least one of $R_1'$ and $R_2'$ is absent; and (iii) when $X_1'$ is N, $R_1'$ when present is Z', or when $X_2'$ is N, $R_2'$ when present is Z'', wherein Z'' is selected from the group consisting of:

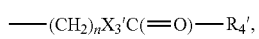

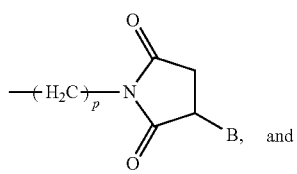

B, and

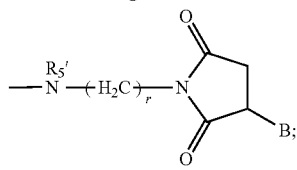

B;

wherein:
n, p, and r are each independently an integer from 1 to 8;
$X_3'$ is O or $NR_6'$;
each $R_3'$, $R_5'$, $R_6'$ and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;
$R_4'$ is —$(CH_2)_m$—B;
wherein m is an integer from 1 to 8; and
B is a binding member having a binding affinity for a ligand or analyte to be detected; and
wherein the biosensor compound exhibits a detectable change in a fluorescence property as a result of binding to the ligand or analyte or as a result of a change in concentration of the ligand or analyte in a sample under test;

(b) contacting the biosensor compound with a sample suspected of containing one or more analytes to bind the one or more analytes, if present, to the binding protein;

(c) irradiating the sample suspected of containing one or more analytes with electromagnetic radiation to induce the fluorophore to fluoresce; and (d) detecting a fluorescence property to determine the presence or amount of one or more analytes in the sample.

In some embodiments of the presently disclosed method, A is coumarin and the biosensor compound of formula A-Y'—B has the following formula:

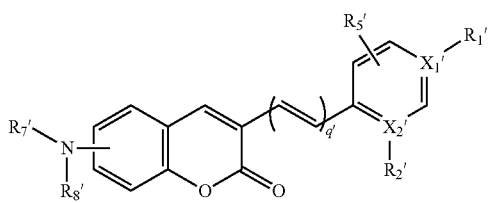

wherein:

q' is an integer from 1 to 8;

each $X_1'$ and $X_2'$ is independently selected from the group consisting of C, S, and N, wherein at least one of $X_1'$ and $X_2'$ is N, under the proviso that (i) when $X_1'$ is C or S, $R_1'$ is Z, or when $X_2'$ is C or S, $R_2'$ is Z, as Z is defined herein below; (ii) if both $X_1'$ and $X_2'$ are N at the same time, at least one of $R_1'$ and $R_2'$ is absent; and (iii) when $X_1'$ is N, $R_1'$ when present is Z", or when $X_2'$ is N, $R_2'$ when present is Z", wherein Z" is selected from the group consisting of:

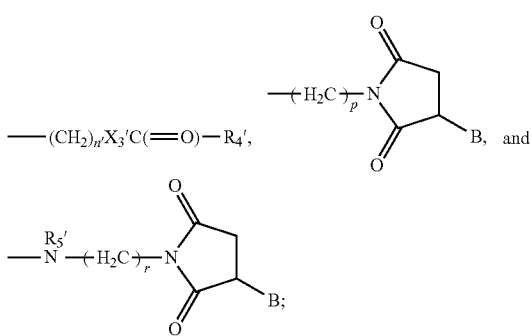

wherein:

n, p, and r are each independently an integer from 1 to 8;

$X_3'$ is O or $NR_6'$;

each $R_3'$, $R_5'$, $R_6'$, $R_7'$, $R_8'$, and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_7'$ and $R_8'$ together represent a $C_2$ to $C_{10}$ alkyl, $C_2$ to $C_{10}$ substituted alkyl, or $C_2$ to $C_{10}$ alkylene;

$R_4'$ is —$(CH_2)_{m'}$—$X_4'$;

wherein m' is an integer from 1 to 8; and

B is a binding member having a binding affinity for a ligand or analyte to be detected.

In some embodiments, the biosensor compound is selected from the group consisting of:

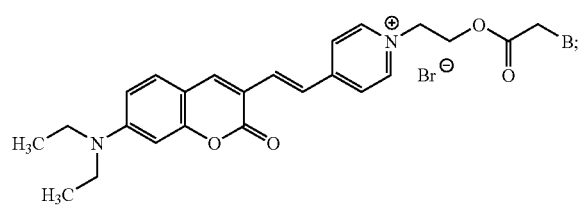

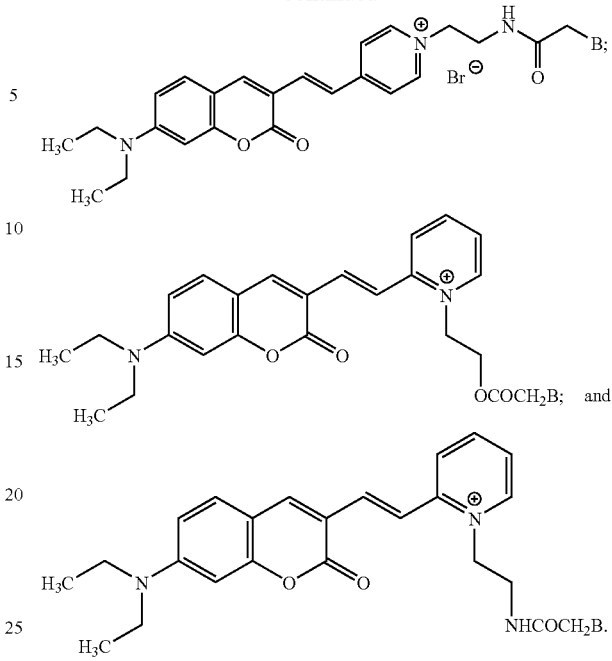

In some embodiments, B is a binding protein as described in more detail hereinabove. In some embodiments, the binding protein is selected from the group consisting of W183C, SM4, and Y10C.

Embodiments that exhibit a shift in emission wavelength upon ligand binding enable a biosensor comprising a presently disclosed fluorophore to be self-referencing. In such embodiments, the fluorophore exhibits an increase in a first emission wavelength in the presence of a metabolite, such as glucose, and a decrease in a second emission wavelength. A ratio between the first emission wavelength and the second wavelength can be calculated to determine the concentration of glucose in the sample under test. Such self referencing can correct for variations in excitation source intensity and other sources of noise and instability in the biosensor without requiring a reference dye. Thus, a single excitation wavelength can be used to observe a ratiometric response in the fluorescence output of the biosensor. As used herein, the term "ratiometric response" means that the intensities of the first emission wavelength and the second emission wavelength vary independently such that the ratio of the two emission wavelengths (the "ratiometric quotient" or "QR") can be used to indicate the presence and/or amount, e.g., concentration, of the ligand or analyte in a sample.

Accordingly, in some embodiments, the presently disclosed method further comprises: (a) measuring a fluorescence intensity at a first emission wavelength before contacting the biosensor compound with a sample suspected of containing one or more analytes; (b) measuring a fluorescence intensity at a second emission wavelength after contacting the biosensor compound with the sample suspected of containing one or more analytes; and (c) determining the ratio of the second emission wavelength to the first emission wavelength to determine the presence or amount of one or more analytes in the sample.

The binding of the one or more target analytes to a fluorophore-binding member conjugate creates or alters a discernable fluorescence property. Discernable changes in the fluorescence property include, but are not limited to, an emission wavelength shift and change, e.g., an increase or decrease, in signal intensity. In some embodiments, the presently disclosed fluorophore-binding member conjugates do not generate a signal when not bound to the target analytes. In other embodiments, the fluorophore-binding member conjugates generate a signal, for example, a first emission wavelength, even when not bound to a target analyte. In such embodiments, the binding of the target analyte, however, still can change the fluorescence property, such that binding is discernable. The binding of the fluorophore-binding member to a target analyte also can cause a decrease in signal intensity.

A detected fluorescence property or a change in the detected fluorescence property due to either a conformational change in the binding protein, subsequent changes in the microenvironment of the fluorescent dye, or both, can be correlated to the presence and/or amount, i.e., analyte concentration, of one or more target analytes. In some embodiments of the presently disclosed method, the mutated binding protein undergoes a conformation change as a result of changes in analyte concentration of the sample suspected of containing one or more analytes. Accordingly, the method detects changes in the fluorescence property as a result of changes in the analyte concentration.

The amount of one or more analytes present in a sample under test can be represented as a concentration. As used herein, the term "concentration" has its ordinary meaning in the art. The concentration can be expressed as a qualitative value, such as negative- or positive-type results, for example, as a "YES" or "NO" response indicating the presence or absence of a target analyte, or as a quantitative value, for example in units of mg/dL. Further, the concentration of a given analyte can be reported as a relative quantity or an absolute quantity. As used herein, "quantitative results" refer to results that provide absolute or relative values.

The quantity (concentration) of an analyte can be equal to zero, indicating the absence of the particular analyte sought or that the concentration of the particular analyte is below the detection limits of the assay. The quantity measured can be the measured signal, e.g., fluorescence, without any additional measurements or manipulations. Alternatively, the quantity measured can be expressed as a difference, percentage or ratio of the measured value of the particular analyte to a measured value of another compound including, but not limited to, a standard or another analyte. The difference can be negative, indicating a decrease in the amount of measured analyte(s). The quantities also can be expressed as a difference or ratio of the analyte(s) to itself, measured at a different point in time. The quantities of analytes can be determined directly from a generated signal, or the generated signal can be used in an algorithm, with the algorithm designed to correlate the value of the generated signals to the quantity of analyte(s) in the sample.

The presently disclosed fluorophores having a reactive group, e.g., a thiol-reactive group, typically exhibit an emission wavelength of about 575 nm or greater. In some embodiments, the presently disclosed fluorophores have an emission wavelength of about 615 nm. Fluorophores having such emission characteristics typically avoid or minimize background interference from the biological system or other components in the analyte, e.g., glucose, source. Further, fluorophores that operate at long emission wavelengths (for example, about 575 nm or greater) can be used as biosensors in vivo. For example, such fluorophores can be incorporated into an implantable biosensor device (with human skin being opaque below about 575 nm).

In the presently disclosed methods for detecting the presence and/or amount of one or more target analytes, the sample suspected of containing one or more target analytes is irradiated with an energy source, such as a laser or light emitting diode (LED), to excite the fluorescent dye. A fluorescence property or a change in a fluorescence property can then be detected.

In some embodiments, a fluorometer can be used to measure the wavelength and/or intensity of fluorescent light. An example of a fluorometer suitable for use with the presently disclosed fluorophores is described in U.S. Published Patent Application No. 2005/0113657, filed Nov. 26, 2003, which is incorporated herein by reference.

The fluorescence and detection can be carried out continuously or intermittently at predetermined times allowing episodic or continuous sensing of an analyte, for example, glucose, to be performed. Thus, the presently disclosed fluorescent dyes are amenable for use with devices capable of continuously measuring the concentrations of one or more analytes. Accordingly, in some embodiments, the method further comprises continuously: (a) contacting the binding protein with the sample suspected of containing one or more analytes; (b) irradiating the sample with electromagnetic radiation; and (c) detecting the fluorescence property. As used herein, the term "continuously," in conjunction with the measuring of an analyte, is used to mean the device either generates or is capable of generating a detectable signal at any time during the life span of the device. The detectable signal can be constant, in that the device is always generating a signal, even if a signal is not detected. Alternatively, the device can be used episodically, such that a detectable signal can be generated, and detected, at any desired time.

The presently disclosed subject matter provides methods which can use specific binding partners for a particular analyte or analytes of interest. A specific binding partner or member, as used herein, is a member of a specific binding pair. A "specific binding pair" refers to two different molecules where one of the molecules through chemical or physical means specifically binds the second molecule. In this sense, an analyte is a reciprocal member of a specific binding pair. Further, specific binding pairs can include members that are analogs of the original specific binding partners, for example, an analyte-analog having a similar structure to the analyte. By "similar" it is intended that, for example, an analyte-analog has an amino acid sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater amino acid sequence identity compared to an analyte amino acid sequence using alignment programs and standard parameters well known in the art. An analog of an analyte also can have the same function as an analyte.

The term "analyte," as used herein, generally refers to a substance to be detected, which can be present or suspected of being present in a test sample. More particularly, an "analyte" can be any substance for which there exists a naturally occurring specific binder partner, such as a binding protein or receptor, or for which a specific binding partner can be prepared. Accordingly, an "analyte" is a substance that can bind one or more specific binding partners in an assay. In some embodiments, the analyte can be any compound, such as a metabolite, to be detected or measured and which has at least one binding site.

The target analytes can be any molecule or compound, of which the presence or amount is to be determined in a sample under test. Examples of classes of analytes that can be measured by the presently disclosed methods include, but are not limited to amino acids, peptides, polypeptides, proteins, carbohydrates, fatty acid, lipids, nucleotides, oligonucleotides, polynucleotides, glycoproteins or proteoglycans, lipoproteins, lipopolysaccharides, drugs, drug metabolites, small organic molecules, inorganic molecules and natural or synthetic polymers. Examples of target analytes include, but are not limited to, glucose, free fatty acids, lactic acid, C-reactive protein and anti-inflammatory mediators, such as cytokines, eicosanoids, or leukotrienes. In some embodiments, the target analytes are selected from the group consisting of fatty acids, C-reactive protein, and leukotrienes. In another embodiment, the target analytes are selected from the group consisting of glucose, lactic acid and fatty acids.

As used herein, the term "carbohydrate" includes, but is not limited to monosaccharides, disaccharides, oligosaccharides and polysaccharides. "Carbohydrate" also includes, but is not limited to, molecules comprising carbon, hydrogen and oxygen that do not fall within the traditional definition of a saccharide—i.e., an aldehyde or ketone derivative of a straight chain polyhydroxyl alcohol, containing at least three carbon atoms. Thus, for example, a carbohydrate as used herein can contain fewer than three carbon atoms.

The term "fatty acids," as used herein include all fatty acids, including free fatty acids (FFA) and fatty acids esterified to other molecules. Examples of specific fatty acids include, but are not limited to, palmitate, stearate, oleate, linoleate, linolenate, and arachidonate. The term "free fatty acid" is used herein as it is known in the art in that FFA are not part of other molecules, such as triglycerides or phospholipids. Free fatty acids also include non-esterified fatty acids that are bound to or adsorbed onto albumin. As used herein, the term "unbound free fatty acid" (unbound FFA) is used to denote a free fatty acid or free fatty acids that are not bound or adsorbed onto albumin or other serum proteins.

As used herein, the term "lipid" is used as it is in the art, i.e., a substance of biological origin that is made up primarily or exclusively of nonpolar chemical groups such that it is readily soluble in most organic solvents, but only sparingly soluble in aqueous solvents. Examples of lipids include, but are not limited to, fatty acids, triacylglycerols, glycerophospholipids, sphingolipids, cholesterol, steroids and derivatives thereof. For example, "lipids" include but are not limited to, the ceramides, which are derivatives of sphingolipids and derivatives of ceramides, such as sphingomyelins, cerebrosides and gangliosides. "Lipids" also include, but are not limited to, the common classes of glycerophospholipids (or phospholipids), such as phosphatidic acid, phosphatidylethanolamine, phosphatidylcholine, phosphatidylserine, phosphatidylinositol, phosphatidylglycerol, and the like.

As used herein, a "drug" can be a known drug or a drug candidate, whose activity or effects on a particular cell type are not yet known. A "drug metabolite" is any of the by-products or the breakdown products of a drug that is changed chemically into another compound or compounds. As used herein, "small organic molecule" includes, but is not limited to, an organic molecule or compound that does not fit precisely into other classifications highlighted herein. More particularly, the term "small organic molecule" as used herein, refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

As used herein, the term "sample" includes any liquid or fluid sample, including a sample derived from a biological source, such as a physiological fluid, including whole blood or whole blood components, such as red blood cells, white blood cells, platelets, serum and plasma; ascites; urine; saliva; sweat; milk; synovial fluid; peritoneal fluid; amniotic fluid; percerebrospinal fluid; lymph fluid; lung embolism; cerebrospinal fluid; pericardial fluid; cervicovaginal samples; tissue extracts; cell extracts; and other constituents of the body that are suspected of containing the analyte of interest. In addition to physiological fluids, other liquid samples, such as water, food products and the like, for the performance of environmental or food production assays are suitable for use with the presently disclosed subject matter. A solid material suspected of containing the analyte also can be used as the test sample. In some instances it might be beneficial to modify a solid test sample to form a liquid medium or to release the analyte.

In some embodiments, the sample can be pre-treated prior to use, such as preparing plasma from blood, diluting viscous fluids, or the like. Such methods of treatment can involve filtration, distillation, concentration, inactivation of interfering compounds, and the addition of reagents.

The sample can be any sample obtained from a subject. The term "subject" refers to an organism, tissue, or cell from which a sample can be obtained. A subject can include a human subject for medical purposes, such as diagnosis and/or treatment of a condition or disease, or an animal subject for medical, veterinary purposes, or developmental purposes. A subject also can include sample material from tissue culture, cell culture, organ replication, stem cell production and the like. Suitable animal subjects include mammals and avians. The term "avian" as used herein includes, but is not limited to, chickens, ducks, geese, quail, turkeys, and pheasants. The term "mammal" as used herein includes, but is not limited to, primates, e.g, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Preferably, the subject is a mammal or a mammalian cell. More preferably, the subject is a human or a human cell. Human subjects include, but are not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. A subject also can refer to cells or collections of cells in laboratory or bioprocessing culture in tests for viability, differentiation, marker production, expression, and the like.

The presently disclosed methods can be used to diagnose, for the prognosis, or the monitoring of a disease state or condition. As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease.

The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition.

As used herein, the term "risk" refers to a predictive process in which the probability of a particular outcome is assessed.

The term "monitoring," such as in "monitoring the course of a disease or condition," refers to the ongoing diagnosis of samples obtained from a subject having or suspected of having a disease or condition.

The term "marker" refers to a molecule, such as a protein, including an antigen, that when detected in a sample is characteristic of or indicates the presence of a disease or condition.

The presently disclosed subject matter also provides methods for monitoring disease states in a subject, including chronic diseases, such as, but not limited to, heart disease, coronary artery disease, diabetes, metabolic disorders, inflammatory diseases, such as rheumatoid arthritis, and cancer. The metabolic disorders can include, but are not limited to, hyperlipidemia, hypolipidemia, hyperthyroidism, and hypothyroidism.

Further, the presently disclosed methods can be used to monitor specific markers of a chronic disease. By monitoring the concentrations of molecular artifacts, metabolites, and deleterious and/or beneficial molecules of a disease state, the subject's progression, regression or stability can be assessed, and treatments can, in turn be adjusted or revised accordingly. For example, markers for heart disease that could be monitored in vivo using the presently disclosed biosensors include, but are not limited to, total fatty acids, lactate, glucose, free fatty acids and various cardiotonic agents, such as, but not limited to cardioglycosides and sympathomimetics. Markers of diabetes include, but are not limited to, glucose, lactate and fatty acids. Likewise, markers for coronary artery disease include, but are not limited to, C-reactive peptide and free fatty acids. Generally, markers of various metabolic disorders include, but are not limited to, specific fatty acids.

The presently disclosed fluorescent dyes also are suitable for use in devices for monitoring drug treatment. Indeed, the biosensor could be designed to specifically bind a drug, drug candidate or a drug metabolite. In this manner, the plasma concentration of the drug could be monitored and dosages could be adjusted or maintained based on the concentration measurements provided by the sensor. Accordingly, a pharmaceutical regimen could be individualized for a particular subject, including the use of a biosensor that can specifically and reversibly bind the drug or drug metabolite to determine plasma concentrations of the drug. The concentrations provided by the sensor can then be used to determine the bioavailability of the drug in the subject. The dose of the drug administered to the subject can then be altered to increase or decrease the bioavailability of the drug to the subject to provide maximum therapeutic benefits and avoiding toxicity.

Biosensor devices comprising the presently disclosed fluorophores can be used to simultaneously monitor a variety of metabolites, the measurements of which could be used to profile the subject's metabolic or physical state. For example, during extended periods of strenuous exercise, glucose is broken down in anaerobic processes to lactic acid. The presently disclosed biosensors can be used to determine lactate thresholds of athletes, to maximize the benefits of training and decrease recovery time. Similarly, the biosensors can be used to determine lactate thresholds in soldiers to prevent fatigue and exhaustion and to decrease recovery time. To that end, the presently disclosed biosensors can be used to monitor glucose levels, lactic acids levels and other metabolites during exercise or physical stress.

In some embodiments, the presently disclosed fluorophores can be used with a biosensor device that is capable of conveying a signal, e.g., emitted light, to a detector that is capable of detecting the signal. In some embodiments, the device comprises the detector, whereas in other embodiments, the device does not comprise the detector, i.e., the detector is external to the device. The signal generated by the device can be a direct indicator of the binding of the one or more target analytes to the binding member, e.g., a binding protein or receptor, associated with the fluorophore.

The presently disclosed fluorophores can be used in biosensor devices suitable for use in various settings, including in vivo, in vitro and in situ. Such devices include medical devices or implants for monitoring metabolic substrate levels in a subject. When such devices are implanted in a subject, the implants should be biocompatible such that they produce little or no detectable inflammation/rejection reaction. One approach for rendering the implants more biocompatible comprises coating the implants with biocompatible polymers, such as poly(urethane) elastomers, poly(urea) and poly (vinylchloride). Exemplary biosensor devices are described in U.S. Patent Application Publication No. 2006/0078908, filed Jun. 7, 2005, and U.S. Patent Application Publication No. 2005/0113657, each of which is incorporated herein by reference in its entirety.

Biosensor devices comprising the presently disclosed fluorophores can be used to monitor a condition or disease state in a patient in an acute care facility, such as an emergency room or a post-operative recovery room or a hospital. For example, in embodiments providing a method for monitoring glucose levels in a subject, studies have shown that mortality can be decreased by as much as 30% in post-operative patients when glucose levels are monitored and kept normal. Thus, the presently disclosed biosensor can be used in situations where monitoring glucose or other metabolites is essential to recovery or the overall health of the subject.

The presently disclosed biosensor can be used or adapted for use in strips, implants, micro- and nano-particles, and the like.

II. Chemical Definitions

While the following terms are believed to be well understood by one of ordinary skill in the art, the following definitions are set forth to facilitate explanation of the presently disclosed subject matter. Unless otherwise defined, all technical and scientific terms used herein have the same meaning as commonly understood by one of ordinary skill in the art to which this presently described subject matter belongs.

Throughout the specification and claims, a given chemical formula or name shall encompass all optical and stereoisomers, as well as racemic mixtures where such isomers and mixtures exist.

When the term "independently selected" is used, the substituents being referred to (e.g., R groups, such as groups $R_1$, $R_2$, and the like, or groups $X_1$ and $X_2$), can be identical or different. For example, both $R_1$ and $R_2$ can be substituted alkyls, or $R_1$ can be hydrogen and $R_2$ can be a substituted alkyl, and the like.

A named "R" or "X" group will generally have the structure that is recognized in the art as corresponding to a group having that name, unless specified otherwise herein. For the purposes of illustration, certain representative "R" and "X" groups as set forth above are defined below. These definitions are intended to supplement and illustrate, not preclude, the definitions that would be apparent to one of ordinary skill in the art upon review of the present disclosure.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, amino, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl. Accordingly, the term "heteroalkyl" refers to an alkyl group as defined herein, wherein one or more the carbon atoms with the alkyl group has been replaced by another atom, including, but not limited to, a nitrogen, an oxygen, and/or a sulfur atom, and the like. Such heteroalkyl groups also can be substituted by one or more alkyl group substituents as defined herein.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, such as a 3- to 7-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a straight or branched hydrocarbon of a designed number of carbon atoms containing at least one carbon-carbon double bond. Examples of "alkenyl" include vinyl, allyl, 2-methyl-3-heptene, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to an aromatic ring system, such as, but not limited to a 5- or 6-member ring system, including one or more heteroatoms, which can be the same or different, and are selected from the group consisting of N, O, and S. The heteroaryl ring can be fused or otherwise attached to one or more heteroaryl rings, aromatic or non-aromatic hydrocarbon rings, or heterocycloalkyl rings. Representative heteroaryl ring systems include, but are not limited to, pyridyl, pyrimidyl, pyrrolyl, pyrazolyl, azolyl, oxazolyl, isoxazolyl, oxadiazolyl, thiazolyl, isothiazolyl, imidazolyl, furanyl, thienyl, quinolinyl, isoquinolinyl, indolinyl, indolyl, benzothienyl, benzothiazolyl, enzofuranyl, benzimidazolyl, benzisoxazolyl, benzopyrazolyl, triazolyl, tetrazolyl, and the like.

A structure represented generally by the formula, wherein the ring structure can be aromatic or non-aromatic:

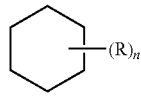

as used herein refers to a ring structure, for example, but not limited to a 3-carbon, a 4-carbon, a 5-carbon, a 6-carbon, and the like, aliphatic and/or aromatic cyclic compound, including a saturated ring structure, a partially saturated ring structure, and an unsaturated ring structure as defined herein, comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure above where n is 0 to 2 would comprise compound groups including, but not limited to:

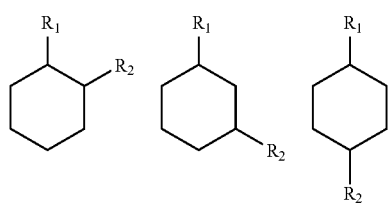

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" refers to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "alkyl-thio-alkyl" as used herein refers to an alkyl-S-alkyl thioether, for example, a methylthiomethyl or a methylthioethyl group.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylamino" refers to an —NHR group wherein R is an alkyl group and/or a substituted alkyl group as previously described. Exemplary alkylamino groups include methylamino, ethylamino, and the like.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino.

"Acylamino" refers to an acyl—NH— group wherein acyl is as previously described. "Aroylamino" refers to an aroyl—NH— group wherein aroyl is as previously described.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Synthesis of ICOPIC Dye

The presently disclosed ICOPIC dye was designed so that the quaternary nitrogen, i.e., the nitrogen atom having a positive charge, is part of an aromatic ring and is farther away from the bridging double bond between the coumarin or aza-coumarin nucleus and the haloacetyl moiety. The IOPIC dye was synthesized as shown in Scheme 1.

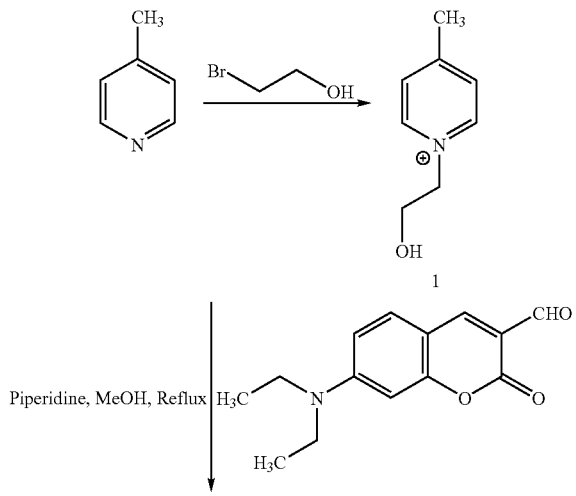

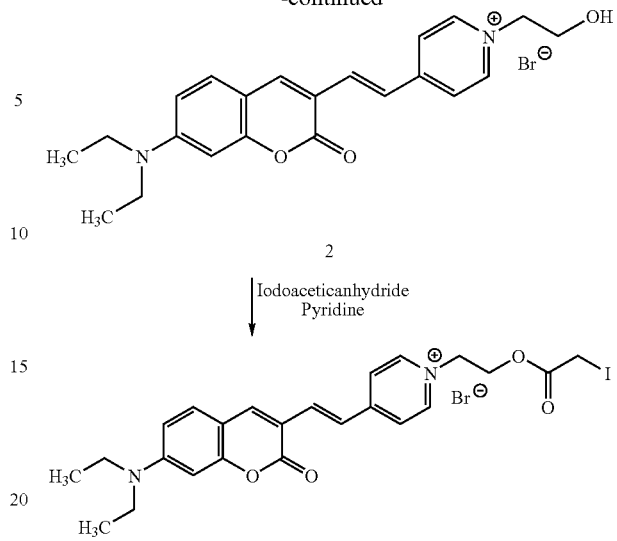

Referring now to Scheme 1, compound 1 was synthesized by reacting 4-picoline and 2-bromoethanol in toluene at 120° C. The reaction was stopped after 45 min, cooled to room temperature, and the toluene layer was decanted out. The obtained light yellow oil was washed with hexane two times and evaporated on a rotary evaporator. The residue obtained was refrigerated to afford a low melting light yellow solid. The product was characterized by $^1$H and $^{13}$C NMR spectroscopy and FAB-mass spectroscopy.

Referring once again to Scheme 1, compound 2 was synthesized as follows. Compound 1 was dissolved in anhydrous methanol and catalytic amount of piperidine was added. The resulting solution was heated to 70° C. for 30 min. During this time the reaction mixture turned to light brown. To this reaction mixture, coumarin aldehyde was added and heated to reflux. After 2 h, the reaction was stopped and then cooled in the refrigerator to afford a red solid, which was filtered and dried. The crude dye was purified by silica gel column chromatography to afford the pure dye. FAB-mass analysis confirmed the product.

Referring once again to Scheme 1, the presently disclosed ICOPIC dye was synthesized as follows. To a solution of compound 2 in a mixture of chloroform and acetonitrile was added 3 drops of pyridine and the obtained solution was stirred at room temperature under argon atmosphere for 10 min. To this reaction mixture iodoacetic anhydride was added and stirring was continued for 2 h at room temperature. After 2 h the reaction was stopped and the solvent was evaporated to obtain a red solid. The obtained solid was washed with MTBE ether and dried under vacuum to afford the ICOPIC as a red solid. The compound was confirmed by FAB-mass spectroscopy and NMR.

Example 2

ICOPIC Labeling Studies

Figure 1:
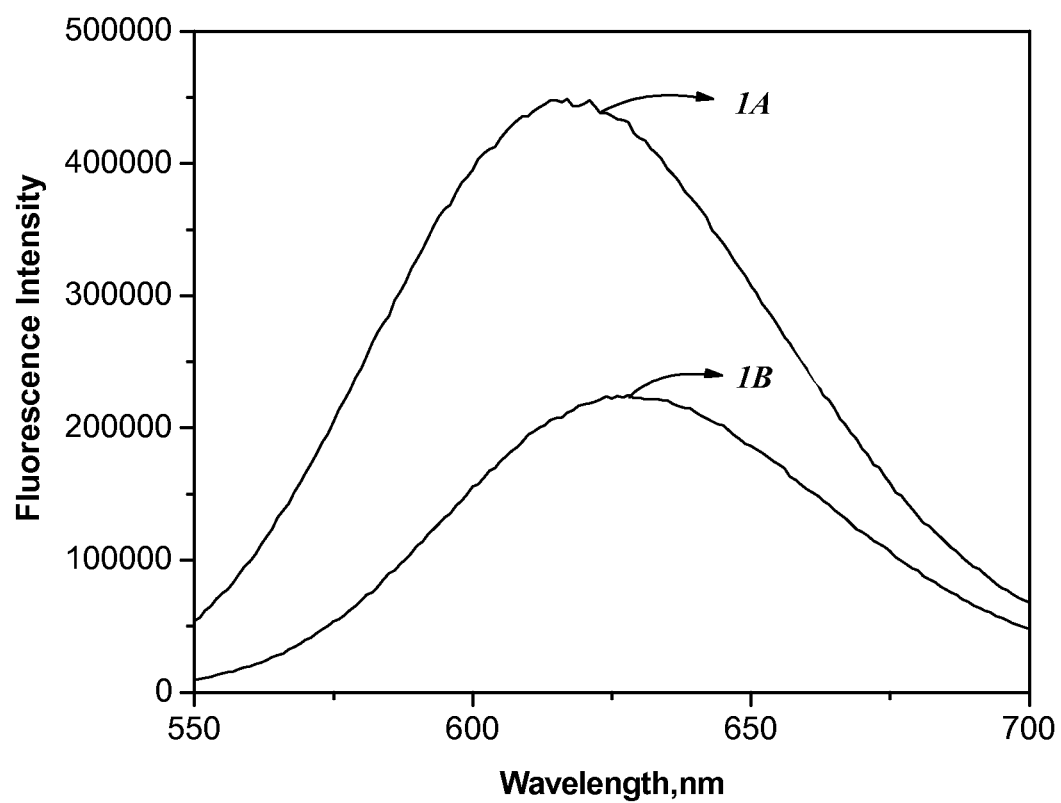

The ICOPIC (ester version) was labeled on glucose binding protein W183C. Referring now to FIG. 1, the ratiometric response to glucose was studied. Referring once again to FIG. 1, the presently disclosed ICOPIC dye responds to glucose ratiometrically and the QR obtained is about 2.0. The QR could be significantly improved by increasing the labeling ratio of the dye to the protein.

Example 3

Temperature Stability

Figure 2:
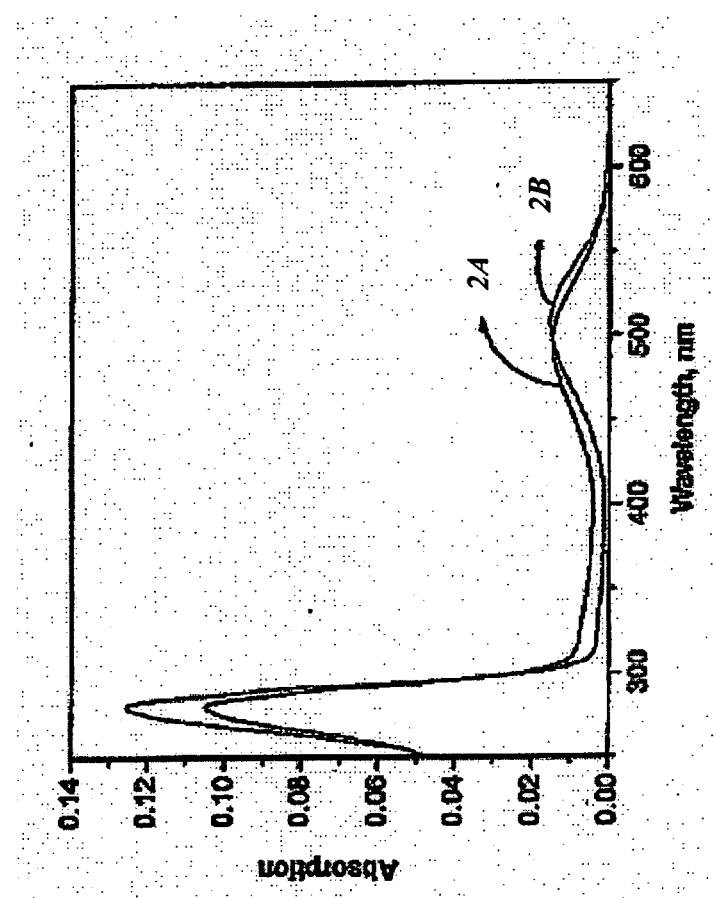

Temperature stability studies of the W183C-ICOPIC conjugate were carried out at 37° C. over 3 days. Referring now to FIG. 2, the dye absorption spectrum remains almost unchanged after 3 days at 37° C. The fluorescence response to glucose, however, was lower (data not shown). Without wishing to be bound to any one particular theory, this observation is likely due to the cleavage of the ester bond and release of the dye from the cysteine residue. The potential release of the dye from the cysteine residue is thought to be minimized in the iodoacetamide version of the dye, as provided in Example 5.

Example 4

Glucose Binding Studies—SM4-o-ICOPIC Ester

Figure 3:
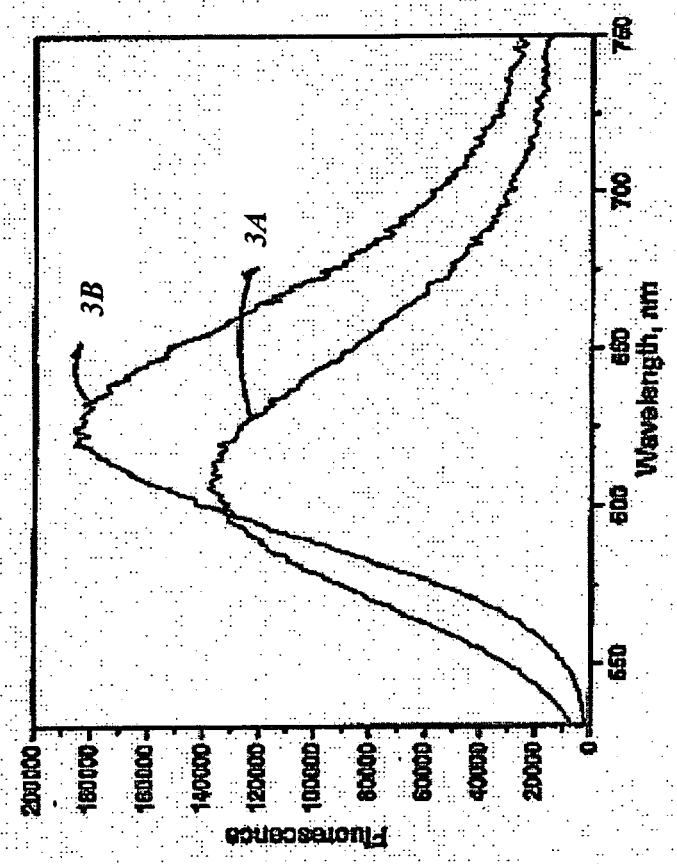

The o-ICOPIC ester dye has been conjugated to SM4 (GBP) protein and the fluorescence response was studied in the absence and presence of glucose. Referring now to FIG. 3, the obtained response is shown. Referring once again to FIG. 3, upon addition of glucose, the spectrum undergoes a 1.5-fold enhancement in fluorescence intensity and a shift in wavelength from about 600 nm to about 625 nm. The QR was calculated and the optimized value was found to be about 7.0. This QR value is the highest QR value observed for any known ratiometric dye with SM4. Accordingly, this dye has significant utility in bio-sensor chemistry.

Example 5

Synthesis of Iodoacetamide—Picoline Dye

To improve the stability of the dye's linker group of ICOPIC, synthesis of an iodoacetamide version of the dye was conducted. The iodoacetamide linker is more stable toward hydrolysis when compared to the iodoacetyl linker group.

One method for synthesizing an iodoacetamide version of the presently disclosed ICOPIC dye is shown in Scheme 2.

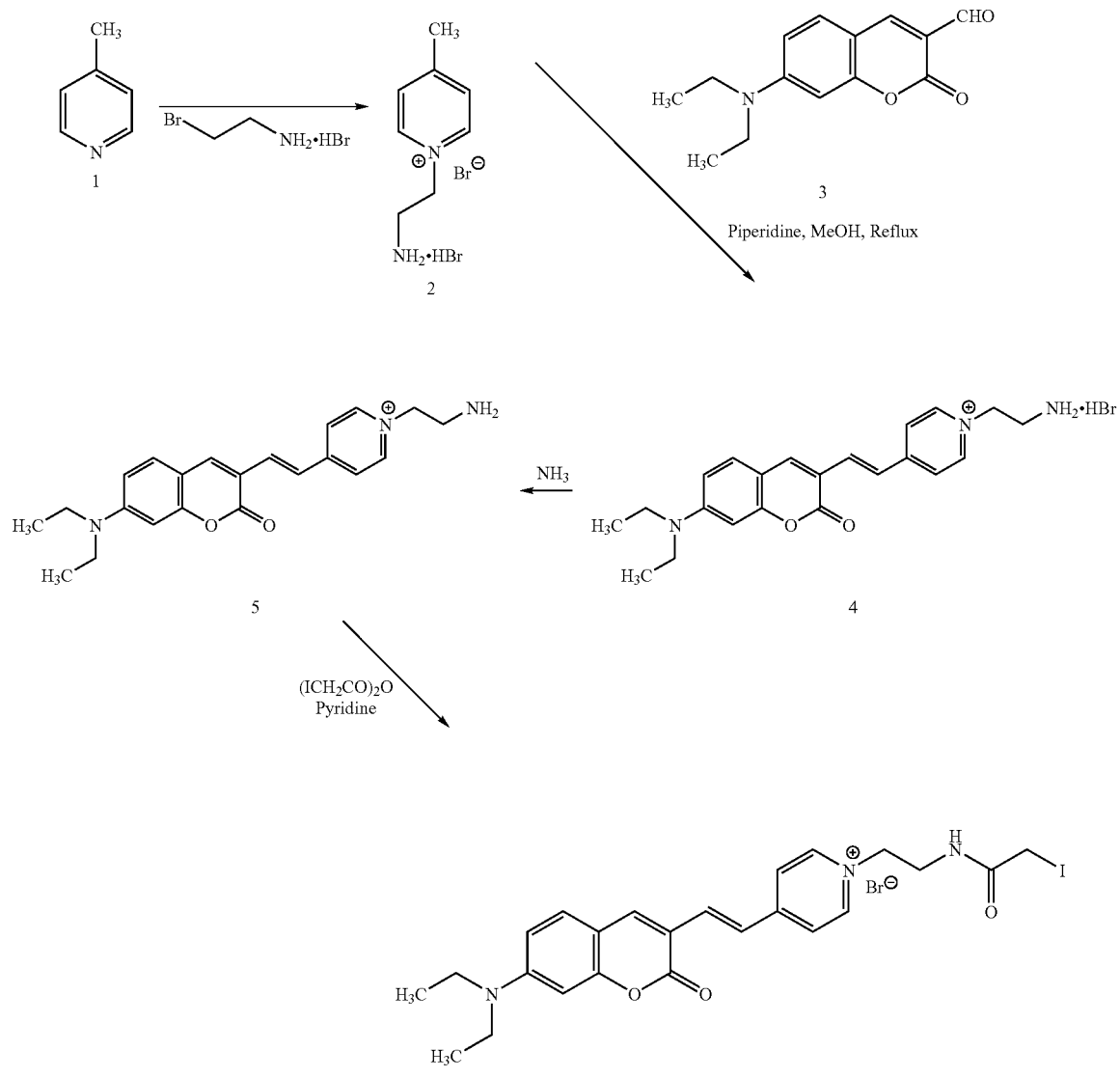

Referring now to Scheme 2, compound 2 was synthesized by reacting 4-picoline with 2-bromoethylaminehydrobromide in methanol under reflux for 48 h. The reaction mixture was cooled to room temperature and the product was precipitated as a white solid. The precipitated product was filtered and washed with cold methanol followed by methyl-tert-butyl ether and dried under vacuum. NMR spectroscopy ($^1$H, $^{13}$C) and FAB-mass spectrum confirmed the structure.

Referring once again to Scheme 2, compounds 4 and 5 were prepared as follows. Compound 2 was dissolved in methanol and catalytic amount of piperidine was added and allowed to reflux for 30 min. The coumarin aldehyde (3) was added and refluxing was continued for an additional 4 h. The progress of the reaction was monitored by TLC. After completion of the reaction the solvent was evaporated to afford a residue. The obtained residue was chromatographed over alumina, eluted with CHCl$_3$/MeOH (6:4) containing a few drops of ammonia solution. The pure product was eluted as a red band and the solvent was evaporated to afford a red dye. Analysis by FAB-mass spectrum confirmed the product.

Referring once again to Scheme 2, the final dye 6, containing the iodoacetamide moiety, was synthesized by reacting compound 5 with iodoacetic anhydride in the presence of pyridine in a mixture of methanol and chloroform. The final dye was purified by washing off the excess of iodoacetic anhydride and pyridine. FAB-mass spectrum confirmed the final dye.

Example 6

Method for Synthesizing p-ICOPIC Amide

An alternative method for synthesizing p-ICOPIC amide is provided in Scheme 3.

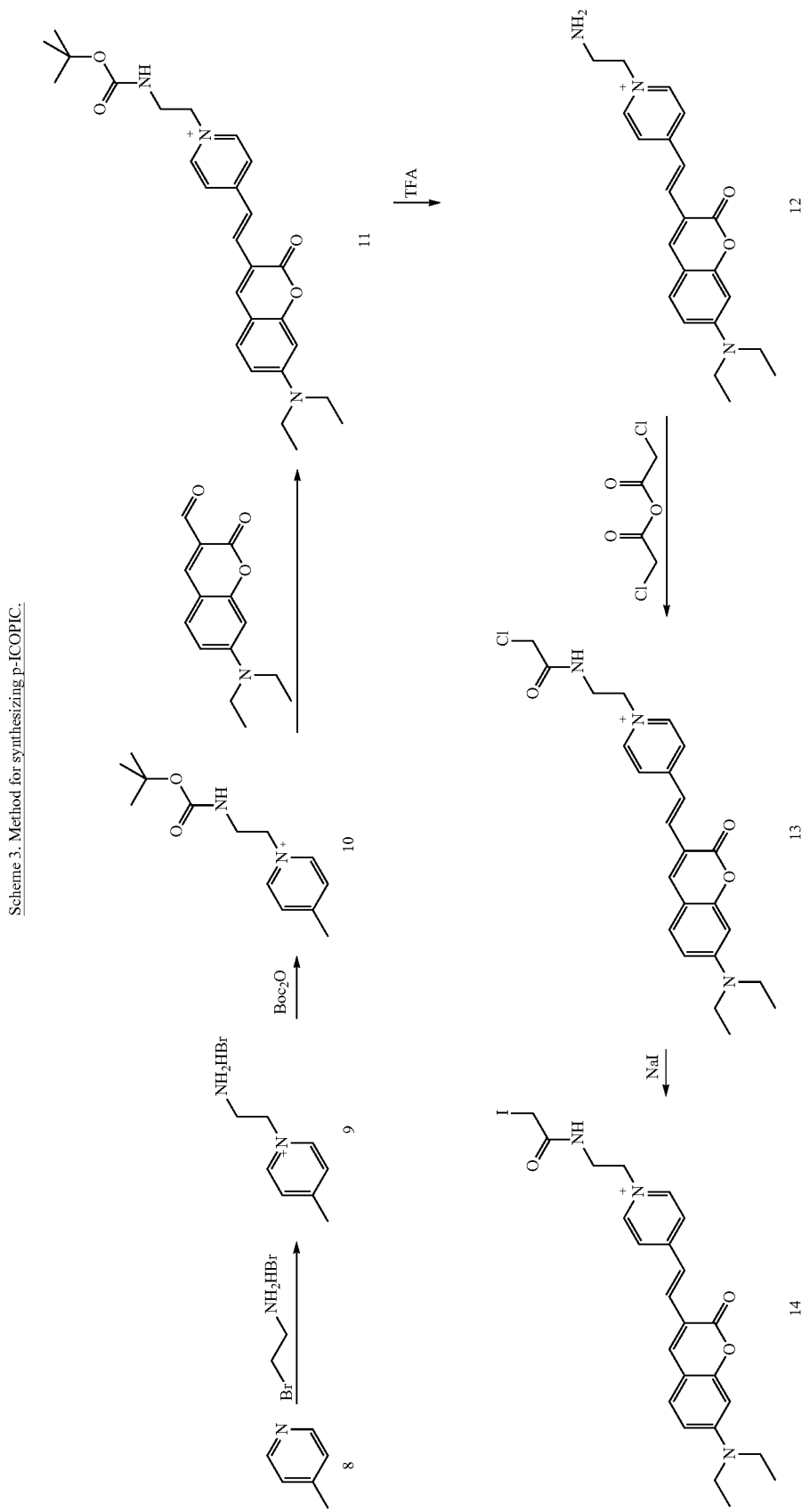
Scheme 3. Method for synthesizing p-ICOPIC.

Referring now to Scheme 3, a presently disclosed p-ICOPIC dye can be prepared as follows.

Compound 9. Compound 8 (4-picoline, 1.0 g) was dissolved in anhydrous methanol (5 mL). Bromoethylamine HBr (2.20 g) was added to the solution. The reaction was heated to reflux and allowed to react overnight. Upon cooling the next day, the product had precipitated. The precipitate was collected by filtration, washed with a small amount methanol and allowed to air dry. The product (1.2 g) was obtained as a colorless solid. The product was confirmed by $^1$H, $^{13}$C NMR and FAB-MS. $^1$H NMR of 9 (400 MHz, CD$_3$OD) δ=8.88 (d, 2H), 8.01 (d, 2H), 4.96 (t, 2H), 3.69 (t, 2H), 2.71 (s, 3H). $^{13}$C NMR of 9 (400 MHz, CD$_3$OD), δ=162.9, 145.3, 130.5, 58.4, 40.5, 22.4. FAB-MS obs=137.1 calc=137.11.

Compound 10. Compound 9 (200 mg) and sodium carbonate (166 mg, 2 eq) were dissolved in 5 mL of H$_2$O. Boc$_2$O (161 mg, 1.1 eq) was dissolved in 5 mL of dioxane and added dropwise to the aqueous solution. The reaction was allowed to stir overnight at room temperature. The next day the solvent was evaporated to dryness leaving a solid white residue. Methanol (10 mL) was added and the resulting solution was filtered to remove the sodium carbonate. The filtrated solution was evaporated to yield 210 mg of product (10) which was used without further purification. The product was confirmed by $^1$H NMR. $^1$H NMR of 10 (400 MHz, CD$_3$OD), δ=8.77 (d, 2H), 7.94 (d, 2H), 4.64 (t, 2H), 3.62 (t, 2H), 2.66 (s, 3H), 1.31 (s, 9H).

Compound 11. Compound 10 (190 mg) and 7-diethylamino-coumarin-3-aldehyde (140 mg) were dissolved in 6 mL of methanol followed by the addition of 50 μL of piperidine. The reaction was heated to 50° C. and allowed to react overnight with stirring. The solvent was then evaporated and the remaining red residue was purified by column chromatography. The product was eluted with a 10% methanol in dichloromethane solution. Pure fractions were combined and evaporated to yield 72 mg of the desired product (11). The product was confirmed by $^1$H, $^{13}$C NMR and HRMS. $^1$H NMR of 11 (400 MHz, CDCl$_3$), δ=8.87 (d, 1H) 8.06 (s, 1H), 7.93 (d, 1H), 7.68 (d, 1H), 7.63 (d, 1H), 7.39 (d, 1H), 6.55 (d, 1H), 6.36 (s, 1H), 4.90 (t, 2H), 3.75 (q, 2H), 3.40 (q, 4H), 1.23 (s, 9H), 1.18 (t, 6H). $^{13}$C NMR of 11 (400 MHz, CDCl$_3$), δ=160.6, 156.9, 156.7, 154.7, 152.5, 146.4, 144.4, 138.1, 131.1, 123.7, 122.9, 114.1, 110.2, 109.4, 96.9, 80.0, 60.0, 45.4, 41.3, 28.5, 12.8. HRMS observed=464.2551, calculated=464.25

Compound 12. Compound 11 (72 mg) was dissolved in a 1:1 solution of dichloromethane:trifluoroacetic acid and allowed to stir for 1 hr. The red color was quenched instantly after adding the TFA solution. After 1 hr, the solvent was evaporated leaving an orange residue. The residue was dissolved in methanol and evaporated multiple times to remove most of the TFA, at which point the deep red color was present once again. The red residue product was dissolved in a small volume of water, followed by freezing and lyophilization. The product was confirmed by $^1$H, $^{13}$C NMR and HRMS. $^1$H NMR of 12 (400 MHz, CD$_3$OD), δ=8.75 (d, 2H), 8.13 (s, 1H), 8.11 (d, 2H), 7.81 (d, 1H), 7.73 (d, 1H), 7.47 (d, 1H), 6.77 (dd, 1H), 6.53 (d, 1H), 4.84 (t, 2H), 3.66 (t, 2H), 3.51 (q, 4H), 1.23 (t, 6H). $^{13}$C NMR of 12 (400 MHz, CD$_3$OD), δ=163.0, 159.1, 158.0, 155.0, 148.3, 146.2, 140.5, 132.9, 125.9, 124.5, 115.9, 112.4, 111.3, 98.4, 58.9, 46.9, 41.3, 13.6. HRMS observed=364.2025, calculated=364.20

Compound 13. Compound 12 was dissolved in dichloromethane (3 mL) with a few drops of methanol added. Chloroacetic anhydride (10 eq) and pyridine (10 eq) was added to the solution. The reaction proceeded for 2 hrs at which point another 10 eq of chloroacetic anhydride was added. After another 4 hrs, the solvent was evaporated and the reaction mixture was purified by silica chromatography using a methanol/dichloromethane solvent mixture. The desired product was eluted with a 10% methanol/dichloromethane mixture. The product was confirmed by $^1$H and $^{13}$C NMR and HRMS. $^1$H NMR of 13 (400 MHz, CD$_3$OD), δ=8.70 (d, 1H) 8.16 (s, 1H), 8.08 (d, 1H), 7.81 (d, 1H), 7.74 (d, 1H), 7.50 (d, 1H), 6.81 (dd, 1H), 6.57 (d, 1H), 4.64 (t, 2H), 4.06 (s, 2H), 3.84 (t, 2H), 3.55 (q, 4H), 1.26 (t, 6H). $^{13}$C NMR of 13 (400 MHz, CD$_3$OD), δ=169.0, 161.1, 157.0, 155.2, 152.9, 146.0, 144.2, 137.7, 130.7, 123.5, 122.7, 114.1, 110.3, 109.4, 96.4, 59.7, 44.8, 41.8, 40.0, 11.6. HRMS observed=440.1743, calculated=440.17.

Compound 14. The o-ICOPIC chloroacetamide (13) was then converted to the iodoacetamide by simple substitution using sodium iodide (NaI). o-ICOPIC chloroacetamide (compound 9) was dissolved in 3 mL of 1:2 MeOH:Acetone solution. Sodium iodide (5 eq) was added to the mixture. This solution was covered in aluminum foil and allowed to reflux overnight. The following day, another 3 equivalents of NaI was added and allowed to reflux another 24 hrs. The next day, the solvent was evaporated under reduced pressure. The red solid was taken up in dichloromethane with a small amount of MeOH. The insoluble salts were filtered and the filtrate was evaporated once again. The red residue was dissolved in a small amount of 20% MeOH/DCM and added to a large volume diethyl ether with swirling to precipitate the dye. The precipitate was filtered as a red solid. The purified product (compound 7) was confirmed by NMR and HRMS. $^1$H NMR of 14 (400 MHz, CD$_3$OD), δ=8.81 (d, 1H) 8.18 (s, 1H), 8.02 (d, 1H), 7.76 (d, 1H), 7.68 (d, 1H), 7.45 (d, 1H), 6.66 (dd, 1H), 6.47 (d, 1H), 4.77 (t, 2H), 3.85 (q, 2H), 3.70 (s, 2H), 3.46 (q, 4H), 1.23 (t, 6H). $^{13}$C NMR of 14 (400 MHz, CD$_3$OD), δ=170.8, 161.5, 156.9, 155.0, 152.8, 146.1, 144.0, 137.9, 130.9, 123.9, 122.6, 113.9, 110.4, 109.4, 96.8, 58.8, 45.2, 40.0, 12.4, −1.2 ppm. HRMS observed=532.1097, calculated=532.11.

Example 7

Synthesis of o-ICOPIC Dyes

Referring now to Scheme 4, an ester version of the presently disclosed o-ICOPIC dye was prepared as follows:

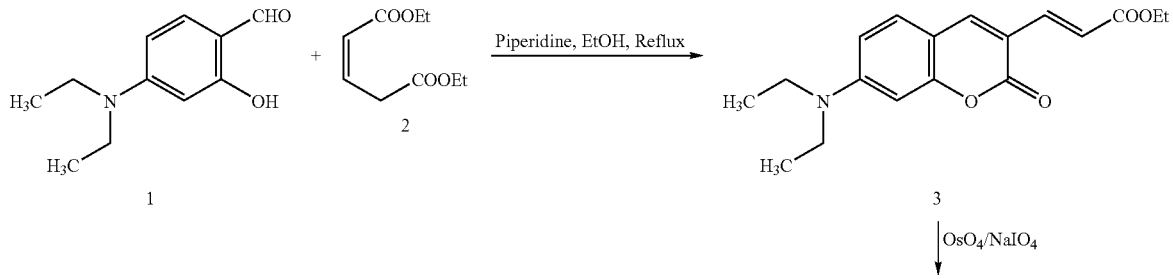

Scheme 4. Synthesis of o-ICOPIC Ester Dyes.

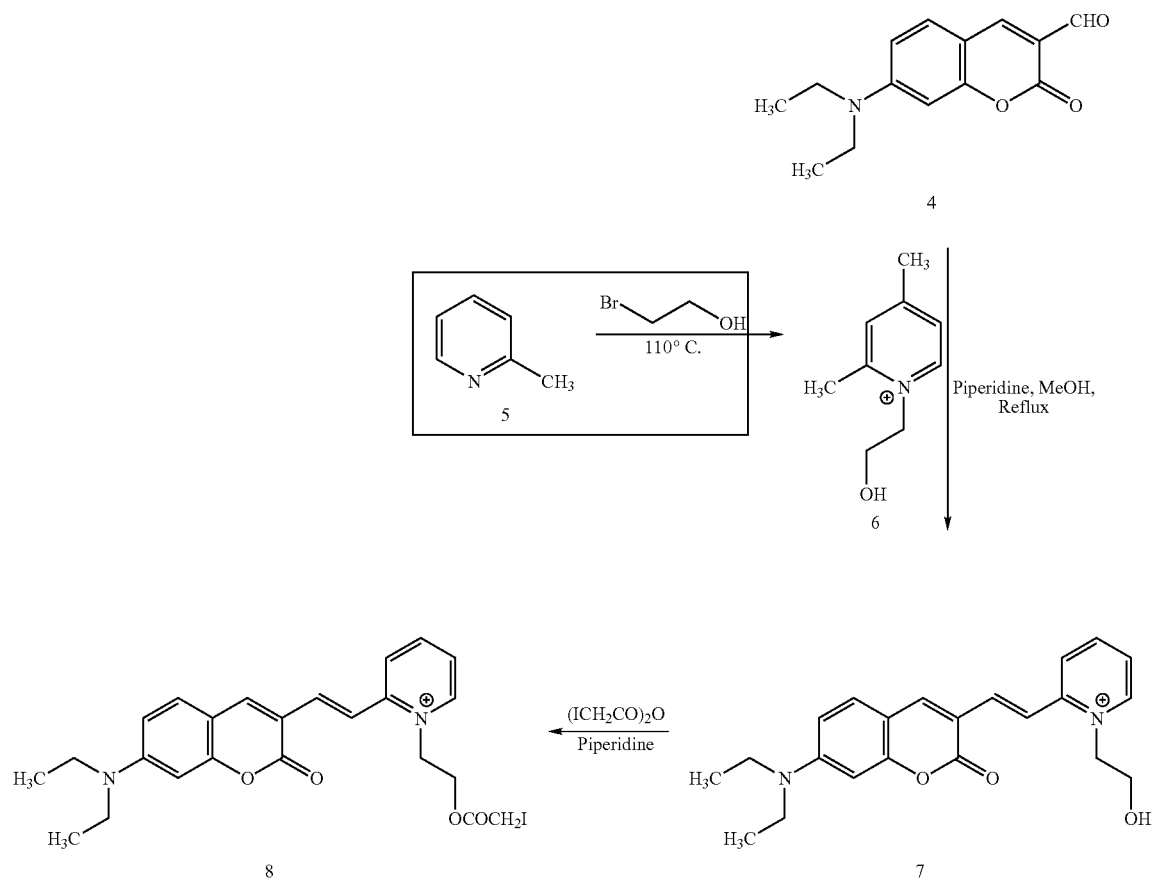
Example 8
Synthesis of o-ICOPIC Amide Dyes
Referring now to Scheme 5, an amide derivative of the presently disclosed o-ICOPIC dye is synthesized as follows:
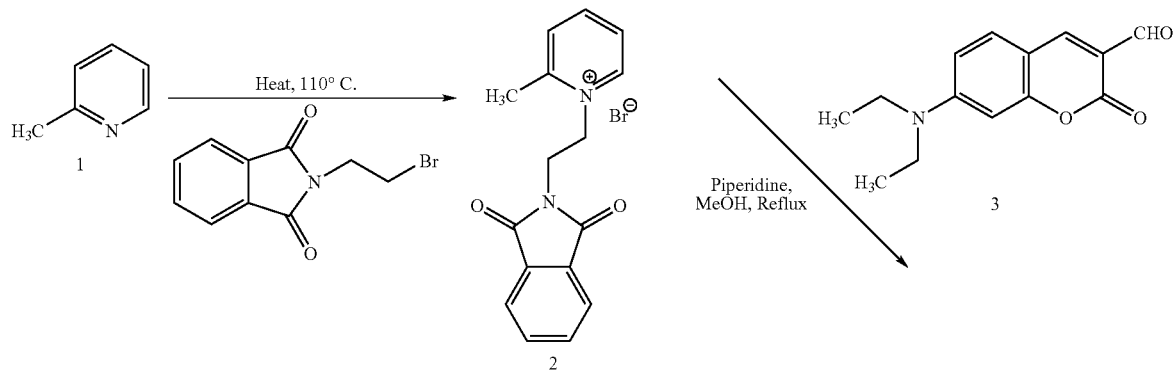

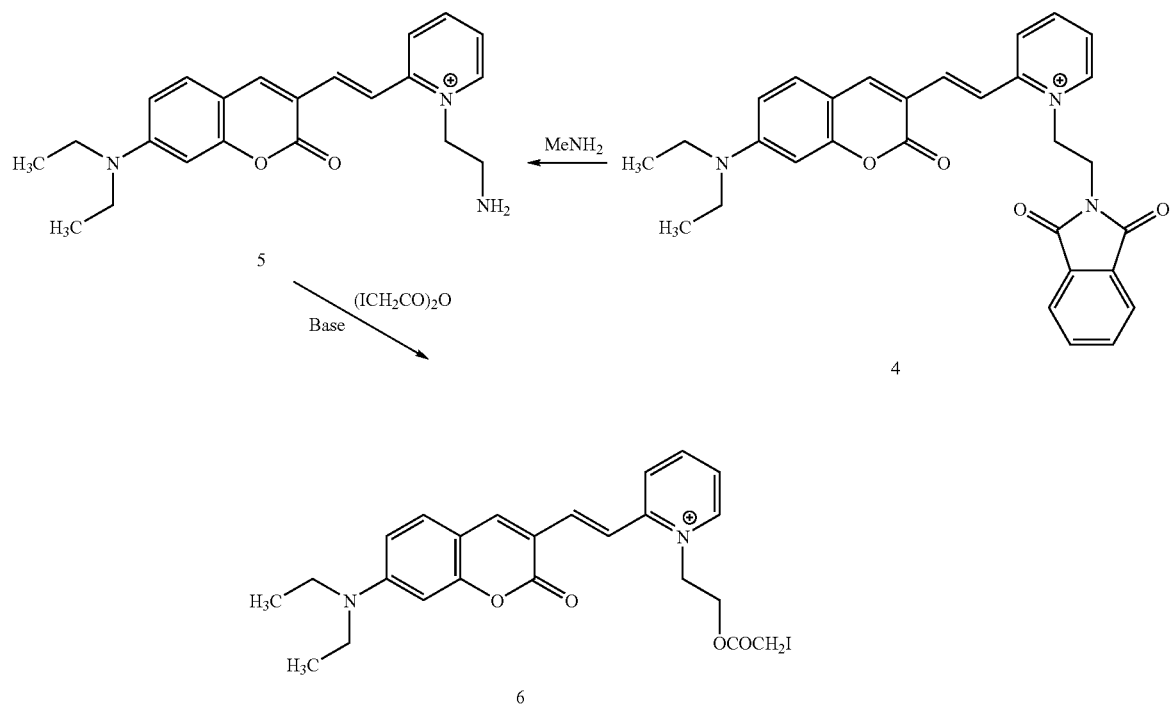
Example 9
Synthesis of Amide Version of o-ICOPIC
An alternative method of synthesizing an amide version of the presently disclosed o-ICOPIC dye is provided in Scheme 6.

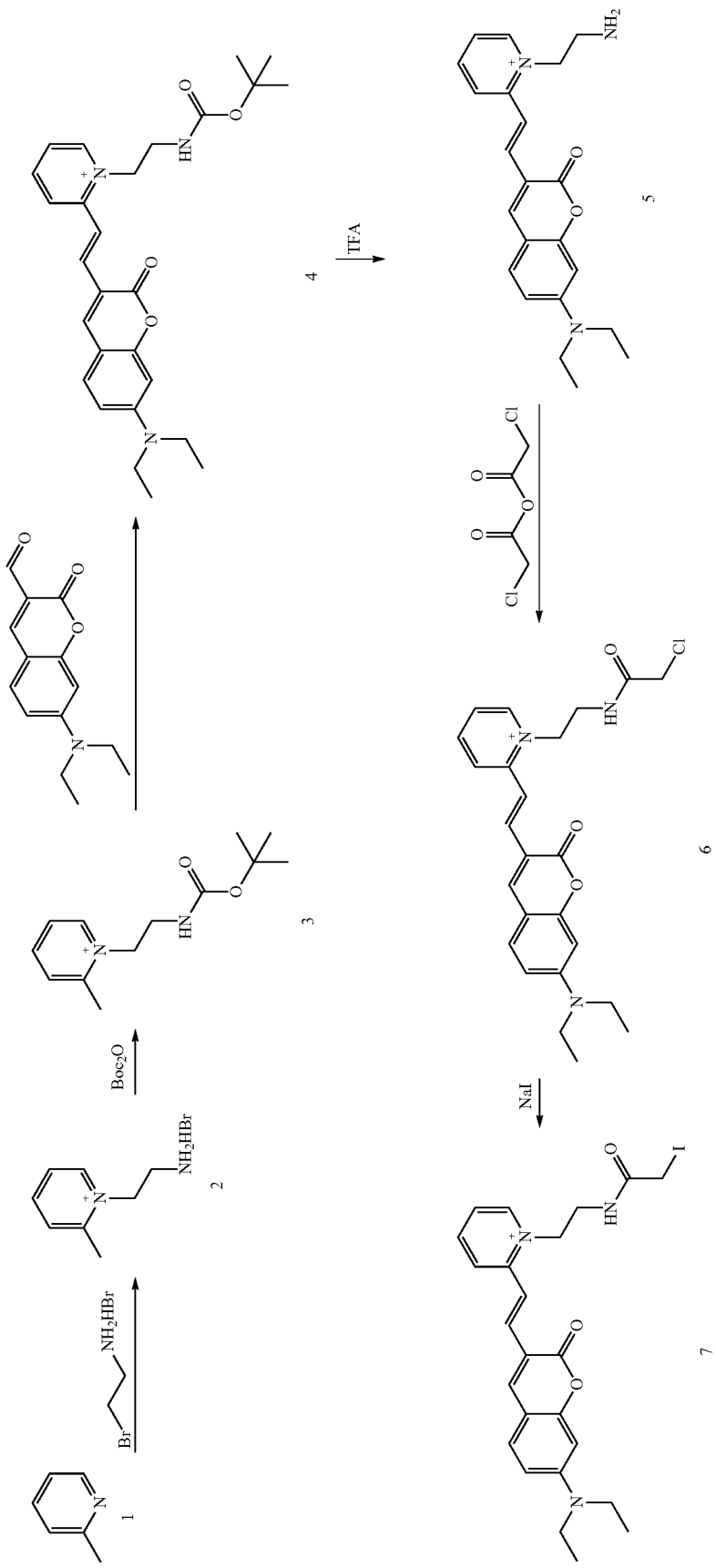

Referring now to Scheme 6, a method of synthesizing an amide version of the presently disclosed o-ICOPIC dye is provided.

Compound 2. Compound 1 (2-picoline, 1.0 g) was dissolved in anhydrous methanol (5 mL). Bromoethylamine HBr (2.20 g) was added to the solution. The reaction was heated to reflux and allowed to react overnight. Upon cooling the next day, the product had precipitated. The precipitate was collected by filtration, washed with a small amount of methanol and allowed to air dry. The product (1.05 g) was obtained as a colorless solid. The product was confirmed by $^1$H NMR. $^1$H NMR of 2, (400 MHz, CD$_3$OD) δ 9.03 (d, 1H), 8.50 (d, 1H), 8.07 (d, 1H), 8.00 (t, 1H), 4.99 (t, 2H), 3.64 (t, 2H), 2.98 (s, 3H).

Compound 3. Compound 2 (200 mg) and sodium carbonate (166 mg, 2 eq) were dissolved in 5 mL of H$_2$O. Boc$_2$O (161 mg, 1.1 eq) was dissolved in 5 mL of dioxane and added dropwise to the aqueous solution. The reaction was allowed to stir overnight at room temperature. The next day the solvent was evaporated to dryness leaving a solid white residue. Methanol (10 mL) was added and the resulting solution was filtered to remove the sodium carbonate. The filtrate was evaporated to yield 190 mg of product (3), which was used without further purification. The product was confirmed by $^1$H NMR. $^1$H NMR of 3 (400 MHz, CD$_3$OD), δ=8.77 (d, 1H), 8.43 (t, 1H), 8.00 (d, 1H), 7.92 (t, 1H), 4.68 (t, 2H), 3.62 (t, 2H), 2.94 (s. 3H), 1.31 (s, 9H).

Compound 4. Compound 3 (190 mg) and 7-diethylaminocoumarin-3-aldehyde (140 mg) were dissolved in 6 mL of methanol followed by the addition of 50 µL of piperidine. The reaction was heated to 50° C. and allowed to react overnight with stirring. The solvent was then evaporated and the remaining red residue was purified by column chromatography. The product was eluted with a 10% methanol in dichloromethane solution. Pure fractions were combined and evaporated to yield 65 mg of the desired product (4). The product was confirmed by $^1$H, $^{13}$C NMR and HRMS. $^1$H NMR of 4, (400 MHz, CDCl$_3$) δ=9.16 (d, 1H), 8.73 (s, 1H), 8.30 (d, 1H), 8.21 (t, 1H), 8.02 (d, 1H), 7.86 (d, 1H), 7.62 (m, 1H), 7.54 (d, 1H), 6.58 (dd, 1H), 6.42 (s, 1H), 5.10 (t, 2H), 3.76 (q, 2H), 3.42 (q, 4H), 1.25 (s, 9H), 1.21 (t, 6H). $^{13}$C NMR of 4, (400 MHz, CDCl$_3$) δ=161.4, 157.4, 156.7, 154.0, 152.8, 146.0, 145.8, 143.7, 140.2, 131.8, 125.0, 124.1, 115.0, 113.8, 109.6, 110.4, 97.1, 79.9, 57.7, 45.5, 40.1, 28.6, 12.8. HRMS of 4 observed=464.2546. calculated=464.25

Compound 5. Compound 4 (65 mg) was dissolved in a 1:1 solution of dichloromethane:trifluoroacetic acid (TFA) and allowed to stir for 1 hr. The red color was quenched instantly after adding the TFA solution. After 1 hr, the solvent was evaporated leaving an orange residue. The residue was dissolved in methanol and evaporated multiple times to remove most of the TFA, at which point the deep red color was present once again. The red residue product was dissolved in a small volume of water, followed by freezing and lyophilization. The product was confirmed by $^1$H, $^{13}$C NMR and HRMS. $^1$H NMR of 5 (400 MHz, CD$_3$OD), δ=8.80 (d, 1H), 8.43 (m, 2H), 8.30 (s, 1H), 7.93 (d, 1H), 7.82 (t, 1H), 7.81 (d, 1H), 7.51 (m, 1H), 6.80 (dd, 1H), 6.53 (dd, 1H), 5.07 (t, 2H), 3.65 (t, 2H), 3.52 (q, 4H), 1.23 (t, 6H). $^{13}$C NMR of 5 (400 MHz, CD$_3$OD), δ=163.3, 159.2, 156.2, 155.2, 149.2, 147.4, 147.1, 143.0, 133.2, 127.7, 126.9, 117.0, 115.3, 112.6, 111.2, 98.4, 56.7, 46.9, 40.0, 13.6. HRMS of 5: observed=364.2022, calculated=364.20.

Compound 6. Compound 5 was dissolved in dichloromethane (3 mL) with a few drops of methanol added. Chloroacetic anhydride (10 eq) and pyridine (10 eq) were added to the solution. The reaction stirred for 2 hrs at which point another 10 eq of chloroacetic anhydride was added. After another 4 hrs, the solvent was evaporated and the reaction mixture was purified by silica chromatography using a methanol/dichloromethane solvent mixture. The desired product was eluted with a 10% methanol/dichloromethane mixture. The product was confirmed by $^1$H and $^{13}$C NMR and HRMS. $^1$H NMR of 6 (400 MHz, CD$_3$OD), δ=8.66 (d, 1H), 8.40 (m, 2H), 8.28 (s, 1H), 8.07 (d, 1H), 7.77 (m, 2H), 7.52 (d, 1H), 6.81 (dd, 1H), 6.57 (s, 1H), 4.82 (t, 2H), 3.99 (s, 2H), 3.84 (t, 2H), 3.54 (q, 4H), 1.24 (t, 6H). $^{13}$C NMR of 6 (400 MHz, CD$_3$OD), δ=169.0, 161.2, 157.1, 154.2, 153.1, 146.7, 145.4, 144.5, 140.0, 131.0, 125.2, 124.5, 115.9, 113.5, 110.4, 109.1, 96.4, 57.3, 44.9, 41.7, 38.9, 11.6. HRMS of 6: observed=440.1743, calculated=440.17.

Compound 7. The o-ICOPIC chloroacetamide (6) was then converted to the iodoacetamide by simple substitution using sodium iodide (NaI). o-ICOPIC chloroacetamide (9) was dissolved in 3 mL of 1:2 MeOH:Acetone solution. Sodium iodide (5 eq) was added to the mixture. This solution was covered in aluminum foil and allowed to reflux overnight. The following day, another 3 equivalents of NaI was added and allowed to reflux another 24 hrs. The next day, the solvent was evaporated under reduced pressure. The red solid was taken up in dichloromethane with a small amount of MeOH. The insoluble salts were filtered and the filtrate was evaporated once again. The red residue was dissolved in a small amount of 20% MeOH/DCM and added to a large volume diethyl ether with swirling to precipitate the dye. The precipitate was filtered as a red solid. The purified product (7) was confirmed by NMR and HRMS. $^1$H NMR of 7 (400 MHz, CD$_3$OD), δ=8.74 (d, 1H), 8.46 (m, 2H), 8.42 (t, 1H), 7.98 (d, 1H), 7.85 (d, 1H), 7.83 (m, 1H), 7.57 (d, 1H), 6.79 (d, 1H), 6.50 (s, 1H), 4.87 (t, 2H), 3.82 (t, 2H), 3.64 (s, 2H), 3.53 (q, 4H), 1.23 (t, 6H). $^{13}$C NMR of 7 (400 MHz, CD$_3$OD), δ=171.0, 161.4, 157.1, 153.8, 153.0, 146.7, 145.5, 144.4, 139.9, 131.1, 125.5, 124.9, 115.7, 113.4, 110.5, 109.1, 96.3, 57.3, 44.9, 41.7, 38.9, 11.8, −3.0. HRMS of 7: observed=532.1097, calculated=532.11.

Example 10

Thermostabilily of Ortho- and Para-ICOPIC Amide

The stability of ortho and para-ICOPIC amide was monitored by both NMR and HPLC, initially at 37° C. for 7 days, followed by incubation at 55° C. for 7 days. Approximately 2 mg of each ICOPIC (1,2) was dissolved in 0.7 mL of CD$_3$OD. The initial NMR spectrum was taken after the sample was prepared and the proton chemical shifts were assigned (color coded below). The prepared samples were then incubated in the NMR tube at 37 and 55° C. for 7 days each. Any change in molecular structure would be evident by loss of a proton peak and formation of a new peak. The NMR spectra in FIGS. 4A-4C (for the para-ICOPIC amide) and 5A-5C (for the ortho-ICOPIC amide) are zoomed on the aromatic region since this is the most susceptible area for reactivity. The spectra show that no significant changes occur in either dye after incubation for 7 days. The NMR experiments also were done with D$_2$O as solvent, which also showed no significant changes in structure (data not shown).

In addition to NMR analysis, the dyes were also analyzed by HPLC at two time points—once when freshly dissolved and second after incubation for 14 days (7 days at 37° C. plus 7 days at 55° C.). The HPLC chromatogram for p-ICOPIC is illustrated in FIGS. 6A and 6B and the HPLC chromatogram for o-ICOPIC is shown in FIGS. 7A and 7B. Once again no new peaks are observed in the chromatogram. Note that the concentrations of the dye samples were not matched before and after incubation at the described temperatures. Thus, the Y-axis scales in FIGS. 6A, 6B, 7A, and 7B are arbitrary and only the position and number of peaks are relevant.

Example 11

GGBP Protein Labeling and Glucose Binding Data
SM4-o-ICOPIC

SM4 (1.2 mg) was mixed with approximately 50 eq. of o-ICOPIC amide. The solution was allowed to react for 4 hrs followed by purification by gel filtration (NAP-10). The UV/Vis spectrum after the labeling is shown in FIG. 8.

The fluorescence of the SM4-o-ICOPIC system was measured in the presence of glucose ranging from 2.5 mM to 200 mM. The resulting spectra show a 25-nm red shift (see FIG. 9A) and they were analyzed ratiometrically using the wavelength ranges of 550-570 nm and 650-670 nm for each spectrum. The ratio points were plotted against glucose concentration to give the hyperbolic binding curve shown in FIG. 9B.

The following tables of values were determined by the hyperbolic fit:

| | | | |
|---|---|---|---|
| $R_0$ | | 0.25 | |
| Kd | | 71.0 | |
| Qr* | | 6.86 | |
| $R_{inf}$ | | 1.71 | |
| | overall | below 200 mg % | above 200 mg % |
| MPE (%) = | 2.2 | 2.4 | 2.1 |

Example 12

GGBP Protein Labeling and Glucose Binding Data
W183C-o-ICOPIC

SM4 (2.0 mg) was mixed with approximately 50 eq. of o-ICOPIC amide dissolved in 20 μL of DMSO. The solution was allowed to react for 4 hrs followed by purification by gel filtration (NAP-10). The UV/Vis spectrum after the labeling is shown in FIG. 10.

The fluorescence of the W183C-o-ICOPIC system was measured in the presence of glucose ranging from 2.5 mM to 200 mM. The resulting spectra show a 25-nm red shift (see FIG. 11A) and they were analyzed ratiometrically using the wavelength ranges of 550-570 nm and 650-670 nm for each spectrum. The ratio points were plotted against glucose concentration to give the hyperbolic binding curve shown in FIG. 11B.

The following tables of values were determined by the hyperbolic fit:

| | | | |
|---|---|---|---|
| $R_0$ | | 0.24 | |
| Kd | | 54.4 | |
| Qr* | | 5.2 | |
| $R_{inf}$ | | 1.25 | |
| | overall | below 200 mg % | above 200 mg % |
| MPE (%) = | 2.0 | 1.6 | 2.2 |

Example 13

GGBP Protein Labeling and Glucose Binding Data
Y10C-p-ICOPIC

A fresh batch of Y10C GGBP (25 mg) was expressed and purified. Y10C (0.6 mg) was mixed with approximately 40 eq. of p-ICOPIC (0.28 mg) amide dissolved in 20 μL of DMSO. The solution was allowed to react for 4 hrs, at which point the progress of the reaction was checked by HPLC. After 4 hrs, only approximately 20% of the protein labeled. Another approximately 40 eq of p-ICOPIC amide was added and allowed to react overnight. The next day, the progress was checked once again by HPLC and the dye:protein ratio was approximately 0.45. The protein was purified by gel filtration (NAP-5). The UV/Vis spectrum after the labeling is shown in FIG. 12.

The fluorescence of the Y10C-p-ICOPIC system was measured in the presence of glucose ranging from 1 mM to 100 mM. The resulting spectra show a 43-nm red shift (see FIG. 13A) with a 5-fold decrease in fluorescence intensity. The spectra were analyzed ratiometrically using the wavelength ranges of 550-570 nm and 700-720 nm for each spectrum. The ratio points were plotted against glucose concentration to give the hyperbolic binding curve shown in FIG. 13B.

The following tables of values were determined by the hyperbolic fit:

| | | | |
|---|---|---|---|
| $R_0$ | | 0.04 | |
| Kd | | 12.0 | |
| Qr* | | 6.7 | |
| $R_{inf}$ | | 0.29 | |
| | overall | below 200 mg % | above 200 mg % |
| MPE (%) = | 8.8 | 14.2 | 4.5 |

Example 14

Fluorescence Intensity of W183C-o-ICOPIC vs. W183C-Acrylodan

The fluorescence intensity of W183C-o-ICOPIC is compared to that of W183C-acrylodan in FIG. 14. As described herein below, the fluorescence intensity of W183C-o-ICOPIC (dye:protein ratio=0.8) is 1.5 times greater than that of W183C-acrylodan (dye:protein ratio=1.2) at a protein concentration of 2 μM. If the dye:protein ratio is factored in, the increase in fluorescence intensity will likely be greater than 2 times for W183C-o-ICOPIC over W183C-acrylodan. The increase in fluorescence intensity can add to increased sensitivity of a sensor. The excitation wavelength for W183C-o-ICOPIC was 485 nm and the excitation wavelength for W183C-acrylodan was 380 nm. All other conditions were the same.

Although the foregoing subject matter has been described in some detail by way of illustration and example for purposes of clarity of understanding, it will be understood by those skilled in the art that certain changes and modifications can be practiced within the scope of the appended claims.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

That which is claimed:

1. A fluorophore, wherein the fluorophore is selected from the group consisting of:

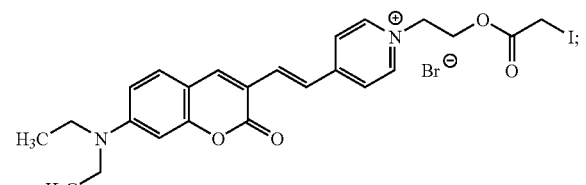

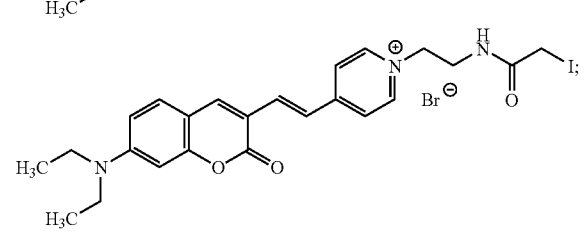

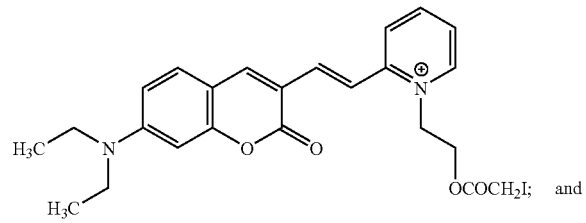

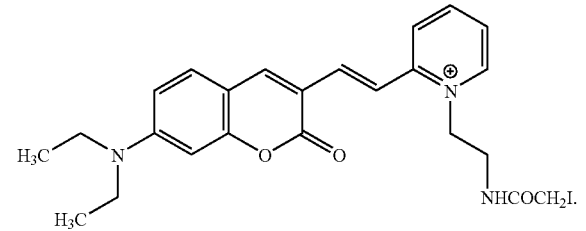

2. A biosensor compound having the following formula:

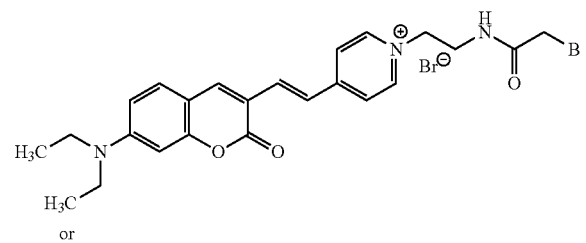

or

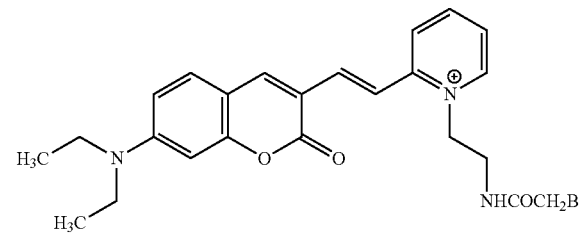

wherein, B is a binding member having a binding affinity for a ligand or analyte to be detected wherein the biosensor compound exhibits a detectable change in a fluorescence property as a result of binding to the ligand or analyte or as a result of a change in concentration of the ligand or analyte in a sample under test.

3. The biosensor compound of claim 2, wherein the binding member is a binding protein.

4. The biosensor compound of claim 3, wherein the binding protein is a periplasmic binding protein.

5. The biosensor compound of claim 4, wherein the binding protein is selected from the group consisting of a glucose binding protein and a glucose/galactose binding protein (GGBP).

6. The biosensor compound of claim 5, wherein the binding protein is selected from the group consisting of W183C, SM4, and Y10C.

7. The biosensor compound of claim 5, wherein the glucose/galactose binding protein has at least one amino acid substitution, and wherein the at least one amino acid substitution is selected from the group consisting of:
(a) a cysteine at position 11;
(b) a cysteine at position 14;
(c) a cysteine at position 19;
(d) a cysteine at position 43;
(e) a cysteine at position 74;
(f) a cysteine at position 107;
(g) a cysteine at position 110;
(h) a cysteine at position 112;
(i) a cysteine at position 113;
(j) a cysteine at position 137;
(k) a cysteine at position 149;
(l) a cysteine at position 213;
(m) a cysteine at position 216;
(n) a cysteine at position 238;
(o) a cysteine at position 287;
(p) a cysteine at position 292;
(q) a cysteine at position 112 and a serine at position 238;
(r) a cysteine at position 149 and a serine at position 238;
(s) a cysteine at position 152 and a serine at position 213;
(t) a cysteine at position 213 and a cysteine at position 238;
(u) a cysteine at position 149 and an arginine at position 213;
(v) a cysteine at position 149 and a serine at position 213 and a serine at position 238; and
(x) a cysteine at position 149 and an arginine at position 213 and a serine at position 238.

8. The biosensor compound of claim 2, wherein the binding member is at least one fragment of a receptor, wherein the receptor is a protein in nature and is capable of binding to a suitable ligand via an active site, and wherein at least one amino acid residue of the fragment is located in a proximity of the active site and is a cysteine residue or is substituted with a cysteine residue.

9. The biosensor compound of claim 8, wherein the receptor has one or more disulfide bridges.

10. The biosensor compound of claim 9, wherein the receptor is an antibody or an antibody fragment.

11. The biosensor compound of claim 10, wherein the receptor is a natural or artificial monoclonal antibody.

12. A method for determining the presence or amount of one or more analytes in a sample, the method comprising:
(a) providing a biosensor compound of claim 2 having at least one mutated binding protein with a fluorophore covalently attached thereto through a thiol group of the mutated binding protein
(b) contacting the biosensor compound with a sample suspected of containing one or more analytes to bind the one or more analytes, if present, to the binding protein;

(c) irradiating the sample suspected of containing one or more analytes with electromagnetic radiation to induce the fluorophore to fluoresce; and (d) detecting a fluorescence property to determine the presence or amount of one or more analytes in the sample.

13. The method of claim 12, wherein the binding member is a binding protein.

14. The method of claim 13, wherein the binding protein is a periplasmic binding protein.

15. The method of claim 13, wherein the binding protein is selected from the group consisting of a glucose binding protein and a glucose/galactose binding protein (GGBP).

16. The method of claim 15, wherein the binding protein is selected from the group consisting of W183C, SM4, and Y10C.

17. The method of claim 15, wherein the glucose/galactose binding protein has at least one amino acid substitution, and wherein the at least one amino acid substitution is selected from the group consisting of:
(a) a cysteine at position 11;
(b) a cysteine at position 14;
(c) a cysteine at position 19;
(d) a cysteine at position 43;
(e) a cysteine at position 74;
(f) a cysteine at position 107;
(g) a cysteine at position 110;
(h) a cysteine at position 112;
(i) a cysteine at position 113;
(j) a cysteine at position 137;
(k) a cysteine at position 149;
(l) a cysteine at position 213;
(m) a cysteine at position 216;
(n) a cysteine at position 238;
(o) a cysteine at position 287;
(p) a cysteine at position 292;
(q) a cysteine at position 112 and a serine at position 238;
(r) a cysteine at position 149 and a serine at position 238;
(s) a cysteine at position 152 and a serine at position 213;
(t) a cysteine at position 213 and a cysteine at position 238;
(u) a cysteine at position 149 and an arginine at position 213;
(v) a cysteine at position 149 and a serine at position 213 and a serine at position 238; and
(x) a cysteine at position 149 and an arginine at position 213 and a serine at position 238.

18. The method of claim 12, wherein the binding member is at least one fragment of a receptor, wherein the receptor is a protein in nature and is capable of binding to a suitable ligand via an active site, and wherein at least one amino acid residue of the fragment is located in a proximity of the active site and is a cysteine residue or is substituted with a cysteine residue.

19. The method of claim 18, wherein the receptor has one or more disulfide bridges.

20. The method of claim 18, wherein the receptor is an antibody or an antibody fragment.

21. The method of claim 19, wherein the receptor is a natural or artificial monoclonal antibody.

22. The method of claim 12, further comprising:
(a) measuring a fluorescence intensity at a first emission wavelength before contacting the biosensor compound with a sample suspected of containing one or more analytes;
(b) measuring a fluorescence intensity at a second emission wavelength after contacting the biosensor compound with a sample suspected of containing one or more analytes; and (c) determining the ratio of the second emission wavelength to the first emission wavelength to determine the presence or amount of one or more analytes in the sample.

23. The method of claim 12, further comprising continuously:
(a) contacting the binding protein with the sample suspected of containing one or more analytes;
(b) irradiating the sample with electromagnetic radiation; and
(c) detecting the fluorescence property.

24. The method of claim 12, wherein the mutated binding protein undergoes a conformation change as a result of changes in analyte concentration of the sample suspected of containing one or more analytes and wherein the method detects changes in the fluorescence property as a result of changes in the analyte concentration.

25. The method of claim 12, wherein the one or more analytes is selected from the group consisting of glucose, a fatty acid, and lactate.

26. A biosensor device comprising the biosensor compound of claim 2.

27. A reagent for determining the presence or amount of one or more analytes in a sample, the reagent comprising a biosensor compound of claim 2.

28. A kit for determining the presence or amount of one or more analytes in a sample, the kit comprising the biosensor device of claim 26.

29. A biosensor compound having the following formula:

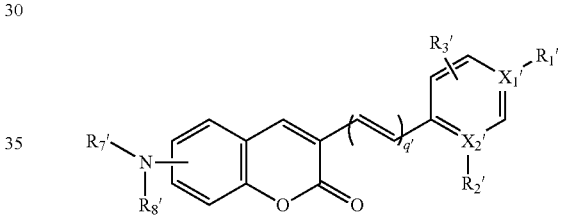

wherein:
q' is an integer from 1 to 8;
each $X_1'$ and $X_2'$ is independently selected from the group consisting of C and N, wherein at least one of $X_1'$ and $X_2'$ is N, under the proviso that (i) when $X_1'$ is C, $R_1'$ is Z, or when $X_2'$ is C, $R_2'$ is Z, as Z is defined herein below; (ii) if both $X_1'$ and $X_2'$ are N at the same time, one of $R_1'$ and $R_2'$ is absent; and (iii) when $X_1'$ is N, $R_1'$ when present is Z", or when $X_2'$ is N, $R_2'$ when present is Z", wherein Z" is —$(CH_2)_n X_3'C(=O)$—$R_4'$, wherein:
n' is an integer from 1 to 8;
$X_3'$ is O or $NR_6'$;
each $R_3'$, $R_6'$, $R_7'$, $R_8'$, and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_7'$ and $R_8'$ together represent a $C_2$ to $C_{10}$ alkyl, $C_2$ to $C_{10}$ substituted alkyl, or $C_2$ to $C_{10}$ alkylene;
$R_4'$ is —$(CH_2)_m$—B;
wherein m' is an integer from 1 to 8; and
B is SM4, wherein SM4 is a mutated glucose/galactose binding protein (GGBP) having the following substitutions: N39I, G82E, Q83K, N84D, Q175E, Q177H, L178M, W183C, N259E and N260S.
30. The biosensor compound of claim 29, wherein the biosensor compound is selected from the group consisting of:
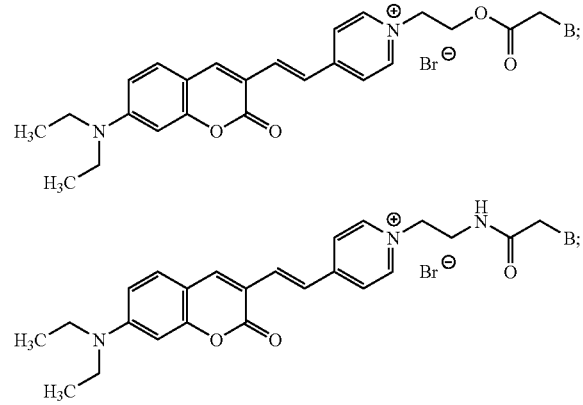
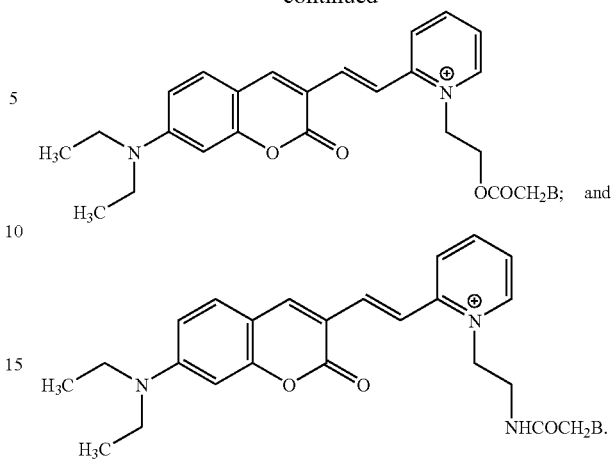
* * * * *